(12) United States Patent
Mangan et al.

(10) Patent No.: US 9,470,637 B2
(45) Date of Patent: Oct. 18, 2016

(54) METHOD AND SYSTEM FOR USE OF BINARY SPATIAL FILTERS

(71) Applicant: Applied Materials Israel, Ltd., Rehovot (IL)

(72) Inventors: Shmuel Mangan, Nes Ziona (IL); Amir Sagiv, Beit-Zayit (IL); Mariano Abramson, Jerusalem (IL)

(73) Assignee: APPLIED MATERIALS ISRAEL, LTD., Rehovot (IL)

( * ) Notice: Subject to any disclaimer, the term of this patent is extended or adjusted under 35 U.S.C. 154(b) by 60 days.

(21) Appl. No.: 14/630,441

(22) Filed: Feb. 24, 2015

(65) Prior Publication Data

US 2015/0233842 A1    Aug. 20, 2015

Related U.S. Application Data

(63) Continuation of application No. 13/536,625, filed on Jun. 28, 2012, now Pat. No. 8,984,453.

(51) Int. Cl.
*G06F 17/50* (2006.01)
*G01N 21/88* (2006.01)
*G01N 21/95* (2006.01)

(52) U.S. Cl.
CPC ...... *G01N 21/8806* (2013.01); *G01N 21/9501* (2013.01); *G01N 2201/068* (2013.01)

(58) Field of Classification Search
CPC ... G02B 27/288; G02F 1/13473; G02F 1/23; G02F 1/13362
USPC .................................. 716/50–55; 430/5, 30
See application file for complete search history.

(56) References Cited

U.S. PATENT DOCUMENTS

| 4,521,075 A | 6/1985 | Obenschain et al. |
| 4,619,508 A | 10/1986 | Shibuya et al. |
| 4,805,123 A | 2/1989 | Specht et al. |
| 4,926,489 A | 5/1990 | Danielson et al. |
| 5,326,659 A | 7/1994 | Liu et al. |
| 5,619,429 A | 4/1997 | Aloni et al. |
| 5,864,394 A | 1/1999 | Jordan, II et al. |
| 6,798,505 B2 | 9/2004 | Karpol et al. |

(Continued)

FOREIGN PATENT DOCUMENTS

WO    2011/029535 A    3/2011

OTHER PUBLICATIONS

Mulder M. et al., "Performance of FlexRay, a fully programmable illumination system for generation of Freeform Sources on high NA immersion system" Proceedings of SPIE, vol. 7640 (2010) pp. 76401P1-76401P10.
Richter R. et al., "AIMS mask qualification for 32 nm node" Proceedings of SPIE, vol. 7488 (2009) pp. 74882R1-74882R11.
Sagiv A. et al., "Aerial Imaging for Source Mask Optimization: Mask and Illumination Qualification" Proceedings of SPIE, vol. 7488 (2009) pp. 74880Z1-74880Z12.

(Continued)

*Primary Examiner* — Nghia Doan
(74) *Attorney, Agent, or Firm* — Kilpatrick Townsend & Stockton LLP

(57) ABSTRACT

Methods and systems for designing a binary spatial filter based on data indicative of a desired exposure condition to be emulated by an inspection system, and for implementing the binary spatial filter in an optical path of the inspection system, thereby enabling emulation of the desired exposure condition by interacting a light beam of the inspection system with the binary spatial filter. The present method and systems enable on-the-fly and on-demand design and implementation/generation of spatial filters for use in inspection systems.

19 Claims, 11 Drawing Sheets

(56) References Cited

U.S. PATENT DOCUMENTS

| | | |
|---|---|---|
| 6,924,891 B2 | 8/2005 | Karpol et al. |
| 7,084,959 B2 | 8/2006 | Albert |
| 7,133,548 B2 | 11/2006 | Kenan et al. |
| 7,321,605 B2 | 1/2008 | Albert |
| 7,463,352 B2 | 12/2008 | Karpol et al. |
| 8,984,453 B2 | 3/2015 | Mangan et al. |
| 2002/0140920 A1 | 10/2002 | Rosenbluth et al. |
| 2006/0164699 A1* | 7/2006 | Inoue .................. H04N 1/4058 358/515 |
| 2012/0008134 A1 | 1/2012 | Azpiroz et al. |

OTHER PUBLICATIONS

Press Release "Carl Zeiss introduces next generation AIMS™ system" Sep. 14, 2009, 2 pages, downloaded from http://www.zeiss.de/C1256A770030BCE0/WebViewTopNewsAIIE/CD 5379230 . . . .

European Search Report for EP13174278.5 mailed Oct. 24, 2013, 7 pages.

Non-Final Office Action of Jun. 3, 2014 for U.S. Appl. No. 13/536,625, 12 pages.

Notice of Allowance of Nov. 5, 2014 for U.S. Appl. No. 13/536,625, 5 pages.

* cited by examiner

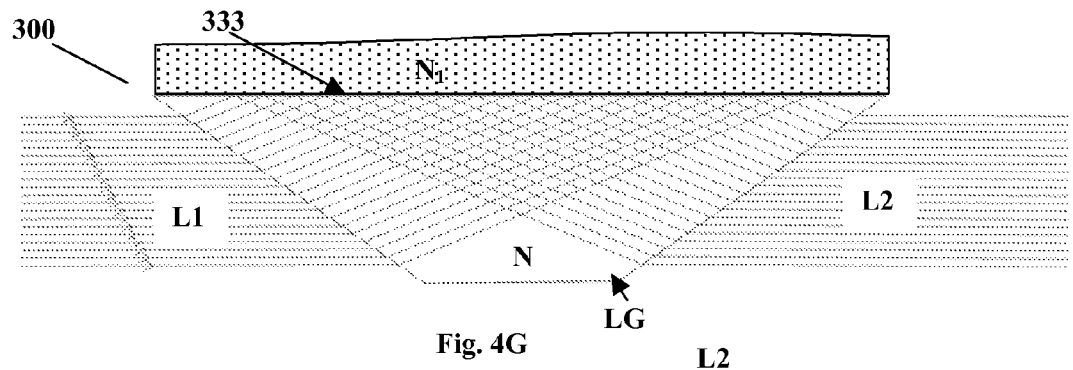
Fig. 4G
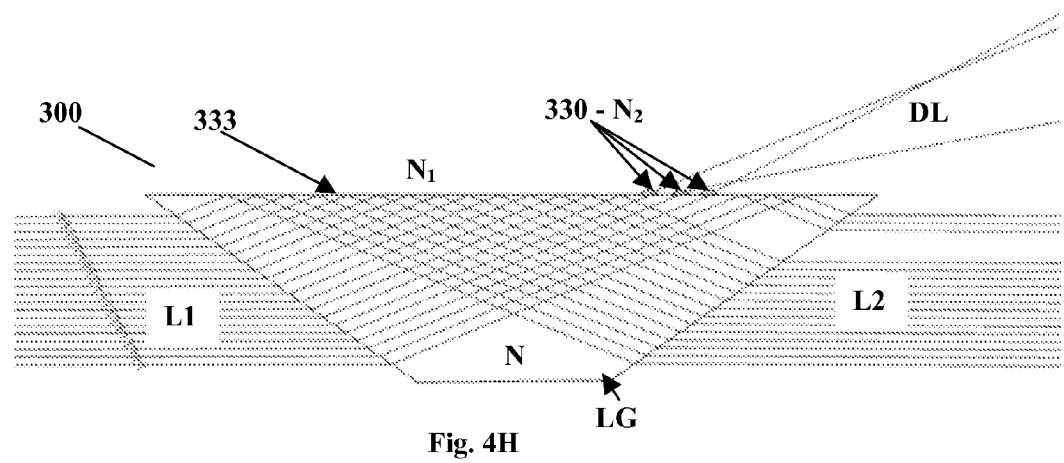
Fig. 4H
Fig. 5A
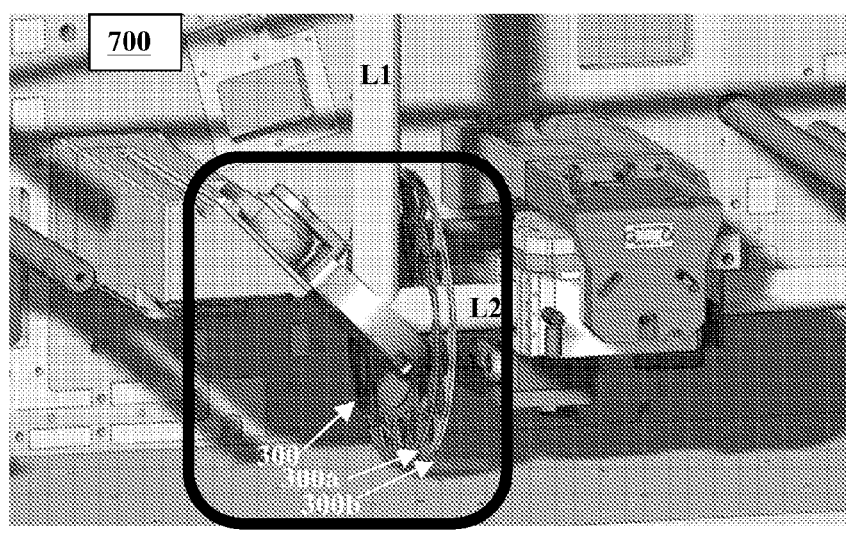

METHOD AND SYSTEM FOR USE OF BINARY SPATIAL FILTERS

CROSS-REFERENCE TO RELATED APPLICATIONS

This application is a continuation of U.S. application Ser. No. 13/536,625, filed Jun. 28, 2012, now issued as U.S. Pat. No. 8,984,453.

FIELD OF THE INVENTION

The present invention is generally in the field of patterning techniques such as photolithography, and relates to a method and system for creation of binary spatial filters, particularly aimed at optimization of spatial filter formation, e.g., for use in aerial imaging.

BACKGROUND OF THE INVENTION

Lithography is a widely used technique for the manufacture of various patterned structures such as integrated circuits, magnetic devices, and other devices. In lithography, a final product is manufactured in a multi-step process, where a "resist" material (sensitive to electromagnetic radiation) is produced for creation of an initial pattern. A pattern is formed in the resist material by exposing different regions of the resist material to different radiation doses. The radiation, e.g., optical radiation in the ultraviolet (UV) or deep UV (DUV) range, or x-rays regimes, is projected through a mask (e.g., reticle) onto the "resist" material.

There are several types of masks that are used in patterning and/or inspection systems. This includes, for example, binary reticles and phase-shift masks. Defects in a mask pattern result in a defected pattern created on an object. Defects in a reticle/mask may be a result of incorrect designing of the mask pattern. Defects may also be generated during a reticle's fabrication process as well as during subsequent processing and handling. A process for manufacturing a reticle/mask is typically similar to an object (e.g., wafer) patterning process. For example, the goal of reticle manufacturing is forming a pattern in an opaque material such as a relatively thin chrome layer on a substantially transparent substrate such as glass (e.g., chrome on glass COG reticles).

Various techniques have been developed for optimizing reticle/mask design and patterning techniques. Some examples of these techniques are described in the following publications:

US 2002/140920 describes a system and method for lithographically printing patterns on a semiconductor using combinations of illumination and mask patterns, which are optimized together to produce the desired pattern. The method of optimizing both illumination and mask patterns allows the development of mask patterns that are not constrained by the geometry of the desired pattern to be printed. Thus, the method provides high quality images even when the desired printed patterns have critical dimensions that approach the resolution limits of a lithographic system. The resulting mask patterns using the method do not obviously correspond to the desired patterns to be printed. Such masks may include phase-shifting technology that use destructive interference to define dark areas of the image and are not constrained to conform to the desired printed pattern.

U.S. Pat. No. 5,326,659 describes a method for making a mask for optical lithography or other projection printing, wherein the mask is represented by a mask pattern. The mask provides a substantially binary output image on the surface of a wafer as light is applied to the mask. Light passes through the mask and onto a wafer at varying intensities, such intensities represented by output intensity values, the threshold values of which produce output images within predetermined constraints. The method includes the steps of defining sampling points, which are representative of the binary output image. These sampling points are used in defining local objective functions, which are combined to give a total objective function.

SUMMARY OF THE INVENTION

The present inventors have determined that there is a need for a novel technique of designing a mask suitable for creating a certain pattern on an object, such as a semiconductor wafer, and also for a technique enabling effective replacement of a mask pattern during the patterning process.

For example, known inspection/patterning techniques (e.g., those used in aerial inspection) utilize a static spatial filter (e.g., source masks) for filtering the inspecting light beam and emulating a desired exposure condition. Such static spatial filters are typically formed utilizing perforated foil structures, chrome on glass (COG) technique or other equivalent techniques. A typical aerial inspection system may accommodate about 15 spatial filters and respectively use them for simulating/producing about 15 exposure conditions. In such systems, replacement of a spatial filter may be a lengthy and, therefore, also costly procedure.

To this end, the present invention provides a complete solution that enables on-the-fly and on demand design and implementation/generation of a spatial filter for use in an inspection system. The invention allows receiving an exposure condition (EC) distribution map, corresponding to a desired exposure condition to be obtained and simulated by the inspection system, and to design and implement corresponding spatial filters that can be used for filtering/masking a light source and generating a light pattern emulating the desired exposure condition.

In this regard it should be noted that different types of inspection systems and particularly aerial inspection systems serve in various different environments, such as a lab environment and production environment, and may accordingly be configured with different performance characteristics. For example, Applied Materials' Aera™ system is an aerial inspection system which may be used in a production environment. In the production environment, an aerial inspection system is typically accommodated along the production line and should provide inspection (e.g., fast inspection) of an extensive area of the inspected object (e.g., inspecting most of the wafer or reticle area) to identify pattern defects in the inspected objects to allow removal of such objects from the production line for further more precise inspection (i.e., review). In production environment, an aerial inspection system, such as the Aera™, is generally required to provide high throughput to facilitate and not delay the production, while providing low rates of miss-identification of defective objects/wafers.

On the other hand, aerial inspection systems may also serve for reviewing wafers in the lab (or outside of the production line) for which a high level of accuracy is required even though there is no requirement for high inspection throughput. Carl Zeiss's AIMS™ is an example of a review system utilizing aerial imaging for reviewing the wafers in environments in which high throughput may not be required.

In many cases, significant delays in the operation of inspection systems in production environments result from the procedure associated with designing/generating an appropriate spatial filter suitable for inspection of the objects/patterns produced on the production line. Additionally, such delays may also occasionally be associated with the introduction and alignment of the spatial filters in the optical path of the inspecting light beam.

As compared with review systems that operate outside the production line, in the production environment less strict light conditions are required for identifying items/objects which might be defective with a low rate of miss-identification of such defective objects. It is noted that in the production line the low rate of defect miss identification is required while moderate rates of false identification may be tolerable since items/wafers that do not pass inspection on the production line are transferred for review (accurate inspection), which is performed outside of the production line.

In this connection, aerial inspection systems are in many cases utilized to inspect reticules, which are used in various steppers for projecting patterns on a photo resist layer of a wafer. To this end, in order to inspect such a reticule for use by a particular stepper, the exposure conditions provided by the inspection system should emulate the exposure conditions of the particular stepper. This is typically achieved by utilizing a spatial filter (source mask) arranged in the optical path of the inspection light beam of the inspection system. The source mask is designed in accordance with the particular stepper for emulating its exposure conditions. As there are many types of steppers, exchange of source masks in the inspection system is typically frequently needed. This is associated with significant delays in the inspection, which may be due to the time required for designing, generating and/or replacing the source mask.

To this end, the inventors of the present invention have found that aerial inspection in production environments may utilize binary spatial filters to emulate desired exposure conditions with sufficient tolerance providing a good rate of identification of defective items and low rates of misidentification of such wafers. For providing low rates of mis-identification of reticule defects, the emulated exposure conditions should only approximate the exposure conditions of the stepper. This is because when only the existence of defects is determined, less strict exposure conditions may be needed, as compared to the strict exposure conditions of a stepper, by which an accurate pattern should be actually printed on a photo resist layer of the wafer. This facilitates the use of binary spatial filters for emulating the desired exposure conditions.

The invention thus provides a system and method for designing and generating/implementing such binary spatial filters, on-the-fly (e.g., by a pattern generation module associated with the inspection system), thus facilitating high throughput in the production line and preventing delays which may be associated with design and generation of the filters upon their introduction to the optical path. Additionally, the invention provides for programmatically designing and implementing a spatial filter (source mask) corresponding to a desired exposure condition. This is achieved by appropriately converting an EC distribution map into a binary spatial filter design indicative of a pattern of spaced apart regions of different transmission properties. This is typically a pattern of regions with substantially opaque and substantially transparent properties with respect to light used in the inspection system (wavelength of light used in the patterning system).

Moreover, the invention allows implementing design of such a binary spatial filter (e.g., binary source mask) on-the-fly as a transient/dynamic filter. This may be achieved, according to the invention, by utilizing a novel beam shaping technique providing a spatial light modulator which may be configured to operate in various wavelength regimes including UV, DUV, X-ray and more.

According to one broad aspect of the invention, there is provided a method for use in creating a binary spatial filter for use in an optical path of an inspection system. The method comprises receiving intensity data indicative of an intensity distribution map corresponding to a desired exposure condition to be emulated by the inspection system; and processing the intensity data, based on predetermined tolerance data, generating filter data indicative of a binary spatial filter, thereby enabling to use the filter data for operating a pattern generation module to create a binary spatial filter.

The input data indicative of an intensity distribution map may actually be represented by a gray level image of the pattern to be obtained on an object being patterned. Preferably, predetermined tolerance data is initially provided, being indicative of an acceptable relation (degree of correlation) between the input intensity distribution map and a pattern obtainable through the binary filter.

In some embodiments, the processing of the intensity distribution map comprises: determining a set of transmission values, which do not exceed a predetermined maximal number of transmission values and associating values of the intensity distribution map with values of the set of transmission values to thereby divide the intensity distribution map into blobs of corresponding transmission values selected from the set of transmission values; and replacing one or more of the blobs with one or more binary transmission patterns having corresponding transmission values, thereby obtaining filter data indicative of the binary spatial filter corresponding to the intensity distribution map. To this end, the tolerance data used in the above processing may include for example any of the following: (i) transmittance tolerance data which is indicative of allowable variations in the transmissions of the blobs (e.g., as compared with the transmission through corresponding regions of the received intensity distribution map), (ii) geometric tolerance data indicative of allowable variations in the geometric shapes of the blobs, and (iii) production tolerance data indicative of the production tolerances of the pattern generation module.

Preferably, the set of transmission values has fewer transmission values than a number of distinct values in the intensity distribution map. For example, the set of transmission values substantially does not exceed six transmission values.

The division of the intensity distribution map into blobs may include replacement of values in the map with the corresponding transmission values from the set of transmission values.

According to some embodiments, the replacement of a blob with a binary transmission pattern is performed utilizing a binary transmission pattern with average or total transmittance that is substantially similar to the average or total transmission value of the blob respectively. In some embodiments, the replacement of a blob with a binary transmission pattern may include inflating or deflating at least one binary transmission pattern, which replaces a blob, such that it has total transmission that is substantially similar to the total transmission through the blob (e.g., similar in accordance with certain predetermined condition(s) specified in the tolerance data).

Each of the one or more binary transmission patterns may be formed by utilizing an arrangement of regions of a first transmission value spaced apart by regions of a second transmission value. In this case, the replacement of a blob with a binary transmission pattern may include configuring the sizes and density of the first and second regions such that the average transmittance through the binary transmission pattern substantially equals the transmission value of a blob to which the binary transmission pattern pertains. The size and density of the first and second regions may be configured such as to reduce at least one of the following effects: diffraction from the binary mask, interference and aliasing of light passing through the binary mask.

In some embodiments, the filter data indicative of the binary spatial filter is used to create the filter in the form of a perforated foil structure.

In some other embodiments, the filter data is used to create the filter in the form of a total internal reflection (TIR) pattern formed by a corresponding liquid pattern deployed on an optical surface. To this end, input light is directed to interact with the optical surface carrying a liquid pattern, to thereby create structured light corresponding to the binary spatial filter.

According to another broad aspect of the invention, there is provided a system for use in creation of a binary spatial filter for an inspection system. The system comprises: an input module configured and operable for receiving intensity data indicative of an intensity distribution map corresponding to a desired exposure condition to be emulated by the inspection system; a processing utility configured and operable for processing the intensity data, utilizing a predetermined tolerance data, and generating filter data indicative of a binary spatial filter; and a patterning controller operable for using the filter data for generating data to operate a pattern generation module to create a corresponding binary spatial filter usable for emulating the desired exposure condition by the inspection system.

The processing utility may comprise a classification module, and a binary pattern design module. The classification module is adapted for processing the intensity data to determine a set of several transmission values not exceeding a predetermined maximal number of transmission values and associate values of the intensity distribution map with values of the set of several transmission values to thereby divide the intensity distribution the map into blobs of homogenous transmission values. The binary pattern design module is configured for replacing/substituting one or more of the blobs with one or more binary transmission patterns, thereby generating filter data indicative of a binary spatial filter having a binary pattern corresponding to said intensity distribution map.

The classification module may utilize a set of transmission values with fewer values than a number of distinct transmission values in said intensity distribution map. The association module may be configured and operable for dividing the map into blobs by replacing values in the map with corresponding transmission values in the association data. The system may utilize tolerance data as indicated above including transmittance tolerance data and/or geometric tolerance data and/or production tolerance data or possibly other types of tolerances which may facilitate adequate design and generation of the binary spatial filter. To this end, in order to determine a design of a spatial filter having a binary pattern corresponding to the intensity distribution map, the processing utility may be configured and operable to modify any of the following in accordance with the tolerance data: (i) the shapes of the blobs; (ii) the transmission values of the blobs; and (iii) the binary transmission patterns substituting the blobs. In this regard, the phrases equal, similar and substantially similar as referred to herein with reference to properties of the binary filter (e.g., shapes of the blobs, transmission values etc.) should be considered in relation to similarity measures/predetermined-condition(s) indicated in the tolerance data.

The binary pattern design module may be configured and operable for replacing at least one blob with a binary transmission pattern having an average or total transmittance that is substantially similar to the average or total transmission of the blob respectively (similar in accordance with allowable tolerances). Alternatively, the pattern creation module may be operable for replacing a blob with a binary transmission pattern and inflating or deflating a binary transmission pattern such that the total transmittance therethrough is substantially similar to total transmission through the blob.

The binary pattern design module may be operable for generating data indicative of a binary spatial filter comprising an arrangement of regions of a first transmission value spaced apart by regions of a second transmission value. In some embodiments, this may be implemented by designing sizes and densities of the first and second regions such that that the average transmittance through the binary transmission patterns in the filter is substantially equal to the respective transmission values of the blobs to which the binary transmission patterns pertain. The binary pattern design module may be operable for configuring the size and density of the first and second regions such as to reduce at least one of the following effects: diffraction from the binary spatial filter, interference and aliasing of light passing through the binary spatial filter.

The system may further include a pattern generation module associated with an optical channel and configured and operable for deploying a liquid pattern corresponding to the binary source mask on an optical surface of the optical channel, thereby enabling creation of a structured light indicative of the binary source mask.

The present invention in yet another aspect provides a method and system for generation of an optical filter. The filter generation method comprises deploying a liquid pattern on an optical surface to form a transient pattern of regions having different critical angles of total internal reflection for light interacting with the regions, corresponding to a desired spatial filter for creation of structured light.

The method may comprise interacting a beam of substantially collimated light rays with the surface such that a fraction of the light rays interacting with the regions undergoes total internal reflection thereby forming structured light corresponding to the desired spatial filter.

The regions from which the light rays are totally reflected may be regions of liquid deployed on the optical surface, or spaces between the liquid regions. The optical surface with the liquid pattern is preferably substantially transparent for the light, thereby reducing light absorption by the surface.

The transient pattern of regions may be selectively removed enabling its replacement by a different pattern. The removal of the liquid pattern may be implemented by clearing the liquid from the optical surface by carrying out at least one of the following: heating the surface for evaporating the liquid, wiping the liquid, blowing the liquid, and changing affinity of the optical surface.

The system of the invention for generation of spatial filters for an inspection system includes a processing utility configured and operable for receiving and processing an intensity distribution map corresponding to a desired exposure condition to be emulated by the inspection system, and a filter generation module configured and operable for receiving the filter data and generating the binary spatial filter indicated thereby in an optical path of the inspection system. The processing may be carried out utilizing predetermined tolerance data corresponding to the inspection system. The processing utility is adapted and is usable for generating filter data indicative of a binary spatial filter for emulating the desired exposure condition. The inspection system thereby enables to emulate the desired exposure condition by enabling interaction of a light beam of the inspection system with the binary spatial filter.

According to some embodiments of the invention, the filter generation module includes a processing module that is configured and operable for processing the filter data to select, in accordance with the tolerance data, a combination of one or more static spatial filters which together form the binary spatial filter. In such embodiments, filter generation module may also include or be associated with a controller module configured and operable for interposing the selected combination static spatial filters in the optical path for emulating the desired exposure condition. Specifically, in some embodiments, the filter generation module includes a carrier module connectable to the controller and configured and operable to enable controllable interposing of one or more static spatial filters in the optical path. The carrier module may include any of the following: (i) a multi wheel carrier assembly including at least two wheels each carrying one or more static spatial filters; and (ii) a cassette assembly configured and operable for carrying multiple static spatial filters and selectively interposing at least one of the multiple static spatial filters in the optical path.

Alternatively or additionally, according to some embodiments of the invention, the filter generation module includes a system for generating transient spatial filters. The system includes an optical surface for carrying a transient liquid pattern, and a liquid deployment module adapted for receiving filter data indicative of a desired spatial filter and deploying, on the optical surface, a corresponding transient liquid pattern forming an arrangement of regions of different critical total internal reflection angles corresponding to the desired spatial filter.

A system of the invention for generation of structured light corresponding to a desired spatial filter comprises: an optical surface exposed to deposition of a transient liquid pattern; a liquid deployment module adapted for receiving filter data indicative of a desired spatial filter and carrying out the deposition of a corresponding transient liquid pattern on the surface forming an arrangement of regions of different critical total internal reflection angles corresponding to the desired filter; and a light port configured and operable for interacting on a beam of substantially collimated light rays with the optical surface, such that a fraction of the light rays undergoes total internal reflection when impinging on the surface, thereby forming structured light corresponding to the desired spatial filter.

DESCRIPTION OF THE DRAWINGS

In order to understand the invention and to see how it may be carried out in practice, embodiments will now be described, by way of non-limiting example only, with reference to the accompanying drawings, in which:

FIGS. 4C to 4H show, schematically, several possible configurations of mask implementations according to the invention.

FIGS. 5A to 5C show, schematically, another example of a filter implementation/generation system configured according to the present invention for pseudo dynamic binary source mask implementation.

DETAILED DESCRIPTION

Figure 1:
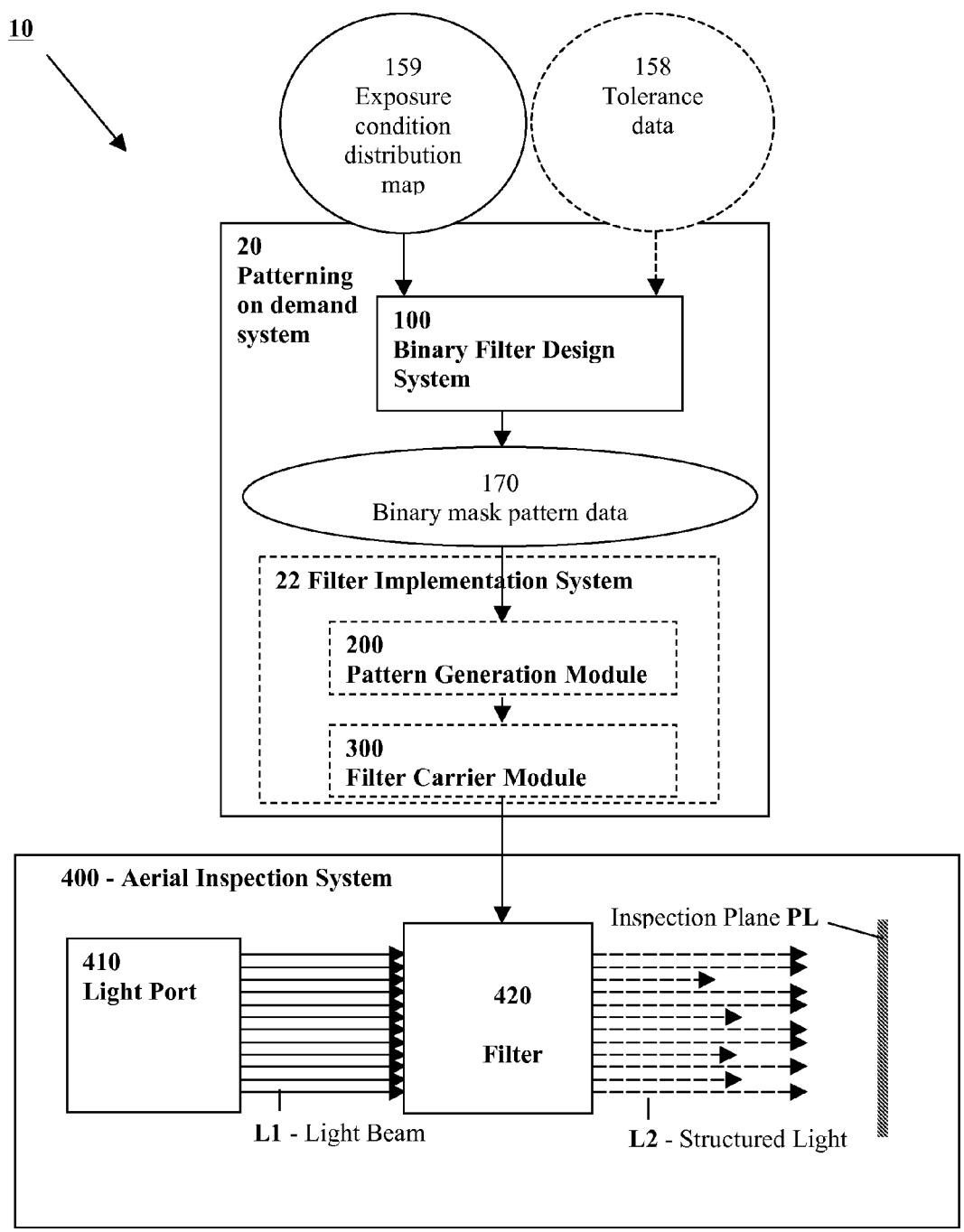
FIG. 1 is a block diagram schematically illustrating an example of a patterning system utilizing a filter/mask design system of the invention for implementing a patterning on demand technique to create a mask used in the patterning system.

According to the present invention, methods and systems are provided allowing patterning on demand of binary spatial filters for use in patterning and inspection systems such as aerial imaging and transient generation of such masks. The invention in its one aspect provides a novel binary filter design system, and in some other aspects provides a novel pattern generation system (e.g., mask creation system) which may or may not utilize the binary filter design system. The principles and operation of the present invention may be better understood with reference to the drawings and accompanying description.

Before explaining exemplary embodiments of the invention in detail, it is to be understood that the invention is not limited in its application to the details of construction and the arrangement of the components set forth in the following description or illustrated in the drawings. The invention is capable of other embodiments or of being practiced or carried out in various ways. As used herein, the phrase "for example," "such as" and variants thereof describing exemplary implementations of the present invention are exemplary in nature and not limiting. Also, it is to be understood that the phraseology and terminology employed herein is for the purpose of description and should not be regarded as limiting.

Referring first to FIG. 1, there is illustrated in the form of a block diagram, an example of a patterning system 10 utilizing a filter design system 100 of the invention for implementing the patterning on demand technique to create a binary spatial filter. System 10 includes a patterning on demand system 20 for generating structured radiation (light) L2 which is further used for patterning/inspection of wafers, reticules or other items. Also shown in the figure is an aerial inspection system 400 which can use the binary filter created by the patterning on demand system 20 and/or may also be used for feedback control of the operation of the binary filter design system 100. Patterning on demand system 20 includes filter design system 100 of the present invention.

Filter design system 100 is configured and operable for receiving intensity data indicative of an intensity distribution map corresponding to a desired exposure condition (EC) and being in the form of an EC distribution map 159 and utilizing this data for generating filter data indicative of a binary pattern of an optimized binary mask to be used for creating a desired light structure. Thus, in the present example, output of the filter design system 100 is directly connected to a pattern generation module 200 of patterning on demand system 20.

It should, however, be noted that the output of the filter design system may be stored in a storage device and used off-line for further filter/mask creation. As for the filter implementation system 22, it may be configured and operable according to the present invention for creating a filter based on a binary filter design pattern, as will be described more specifically further below.

It should be noted here that the terms exposure condition (EC) distribution map, e.g., intensity distribution map, and transmittance condition (TC) distribution map are generally used herein to denote a two dimensional map of values (e.g., scalars or vectors). Such maps may be represented as images (e.g., pixilated images) and accordingly they may be described and referred to below using image terminology (e.g., values in such a map are also referred to as pixels). In certain applications to which the present invention pertains, the values in an EC distribution map are indicative of light intensity distribution to be obtained after the input light passage through/interaction with the mask, e.g., at the imaging plane as can be used/controlled by an aerial imaging/inspection system. The values in a TC distribution map may be indicative of a transmittance/reflectance distribution of a spatial filter/source mask (i.e., in the mask plane), which is designed for emulating exposure conditions as defined in an EC distribution map.

It should also be noted that terms binary pattern, binary map and the like are used herein to denote a two dimensional map which associates each point thereon with one of two values (e.g., with a binary/Boolean value). Such binary patterns may be represented/implemented in dynamic/transient or static masks including for example duo-chromatic/duo-transmissive images, spatial light modulators (SLM) of binary nature (e.g., transmissive/semi-transmissive or transmissive/opaque modulators), patterned screens, perforated foils and also data indicative of such patterns or their digital representations.

In the present example of FIG. 1, patterning system 20 is associated with an aerial inspection system 400, which utilizes an optimized binary spatial filter 420 formed by pattern generation module 200 for reticule inspection. Optionally, the aerial inspection system 400 may also provide a feedback control signal to the filter design system 100. Aerial inspection system 400 includes a light port 410 providing inspection light L1 (typically in the ultra violet (UV) regime or deep UV (DUV) regime) to propagate through the filter 420 towards an object being patterned and/or inspected located at inspection/imaging plane PL.

Filter implementation system 22 typically includes a filter carrier module 300 used to hold the filter in the propagation path of light L1 such that after light L1 interacts with the filter 420 it forms patterned/structured light L2 propagating to the inspection plane PL.

As will be described further below, the filter carrier module 300 may be configured according to the invention for selectively providing interaction of light L1 with a desired spatial filter. The latter may be a dynamic/pseudo-dynamic filter/mask created by the pattern generation module 200 of the invention. Pattern generation module 200 may be configured and operable in accordance with the wavelength regime(s) used by aerial inspection system 400, and is adapted for implementing/generating optimized binary spatial filter (420) capable of structuring/patterning light in these wavelength regimes (e.g., masking the UV or DUV radiation).

The filter design system 100 is configured and operable for receiving a desired EC distribution map 159 and designing a corresponding binary spatial filter pattern 170 (e.g., binary mask). The binary mask pattern 170 can then be implemented by filter implementation system 20 to create structured light L2 approximating the desired EC distribution 159. Optionally, filter design system 100 is also configured for receiving tolerance data 158 and is adapted to utilize that data for designing the pattern of the binary spatial filter such that a difference between the structure/pattern of light beam L2 and the desired EC distribution 159 is within an acceptable tolerance level provided in tolerance data 158. As noted above, patterning on demand system 20 may also be associated with a pattern generation module 200 (or a driver thereof) allowing on demand implementation of an optimized binary spatial filter 420 based on a binary filter pattern 170. To this end, the optimized binary spatial filter 420 may be implemented by utilizing any known light patterning technique suitable for operating at desired wavelengths. For example, pattern generation module 200 may be configured and operable of implementing/generating filter 420 as a static mask by patterning the mask on a foil (i.e., perforated foil PF mask) and/or by patterning chrome on a glass COG mask.

In case of static masks, filter carrier module 300 may be configured for carrying/embedding one or more of such mask(s). An example of filter carrier module 300 adapted for carrying static masks and interposing a selected one of them in the optical path of a light source is known in the art as a sigma wheel module. A sigma wheel module is typically capable of carrying several static masks along its perimeter and is mounted for rotation about its central axis. Rotation of the sigma wheel allows engagement of a selected mask to interact with light impinging on the wheel. According to the invention, a controller unit may be associated with such a sigma wheel tool and may be configured and operable for receiving a desired binary filter design from the system 100 and switching/rotating the sigma wheel to locate the most suited static mask (which best approximates the desired binary mask pattern 170) in the optical path of light propagating towards the wheel's plane.

Considering creation of a dynamic (i.e., transient) spatial filter 420, this may be implemented by utilizing a spatial light modulation technique provided by the present invention. When configured according to this technique, filter implementation system 22 is capable of on-the-fly generation of transient binary spatial filters which may be adapted for masking/filtering light in various wavelength regimes including the UV and/or DUV regime. Embodiments of a filter implementation technique of the invention will be described below with reference to FIGS. 4A to 4H and FIGS. 5A to 5C.

Figure 2A:
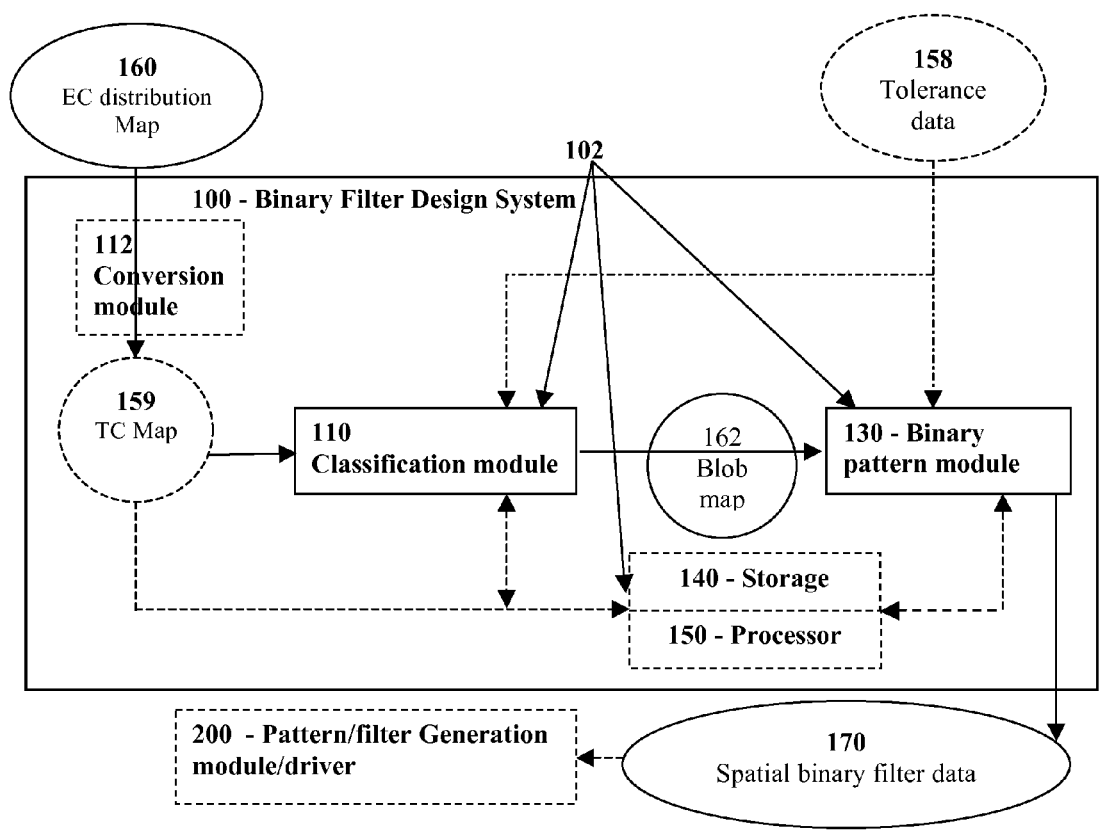
FIGS. 2A and 2B exemplify the configuration of a filter/mask design system and a method for designing patterns of binary spatial filters (e.g., binary source masks).

Reference is now made to FIG. 2A illustrating schematically, in the form of a block diagram, the configuration of a filter design system 100 according to the present invention. Common elements and features of the invention having similar purpose or functionality are identified by the same reference numerals in all the figures.

System 100 is configured as a computer system including inter alia such utilities/modules as data input and output utilities (not shown); processor utility 102 for processing the input data and generating output data indicative of a binary spatial filter; and also preferably includes internal memory utility 140. The system 100 is thus configured and operable for receiving/utilizing an input data indicative to the intensity distribution map or EC distribution map 159, and processing the input EC distribution map 159 (preferably utilizing a predetermined tolerance data) to produce a filter data 170 corresponding to a binary spatial filter design/pattern. Possibly, the filter data 170 is then transferred to a storage device or to a pattern generation module 200 (or to a driver associated therewith) and is further used to generate a corresponding binary spatial filter.

In some embodiments, the processor utility 102 includes a conversion module 112 which performs a preliminary processing of the input EC distribution map 159 to convert the map data 159 into a transmittance distribution map data 160 indicative of desired distribution of optical properties to be obtained in the pattern of the binary spatial filter (filter data 170). Examples of EC distribution map 159 and a filter data 170, derived therefrom utilizing the technique of the present invention, are graphically illustrated respectively in FIGS. 3A and 3F.

The processor utility 102 includes classification module 110 which is adapted for processing data indicative of the received EC distribution map (e.g., in the form of the transmittance distribution map 160), and generating a blobbed transmittance map 162 formed with blobs of homogeneous transmittances. The processor utility 102 also includes a binary pattern module 130 configured for analyzing the blobbed transmittance map and replacing blobs in the blobbed map 162 with binary patterns (e.g., with data indicative thereof), to thereby generate output filter data 170 indicative of a pattern of a binary spatial filter corresponding to the EC distribution map 159.

Optionally, in some embodiments of the present invention, the processor utility 102 of system 100 may also include a general processing unit 150 (e.g., processor) and a memory utility 140 which may be utilized by any of modules 110 and/or 130 for carrying out various types of data processing. The memory utility 140 may be used for storing various types of data, such as reference data (e.g., tolerance data), input EC map, as well as output filter data) and/or for communicating data (directly or indirectly) between the modules and external devices such as an external storage device and a pattern generation module 200 or a driver thereof.

As indicated above, the input EC distribution map 159 may typically represent a desired structure (e.g., intensity distribution, exposure/illumination pattern) of light L2 to be used in creation of a binary spatial filter/mask intended for use in specific patterning/inspection applications. A TC distribution map 160 may be derived from the EC distribution map 159 (e.g., utilizing conversion module 112 described below). Alternatively or additionally, the input EC distribution map 159 may by itself include or be indicative of a TC distribution map 160 corresponding to a desired design of a spatial-filter/source-mask. In this regard, the EC distribution map 159 is indicative of a TC distribution map 160 (i.e., being a non binary map) which should be approximately implemented by binary spatial filter indicated by filter data 170.

For example, in some embodiments of the invention, EC distribution map 159 is indicative of a desired illumination pattern/structure at an optical plane spaced from the plane of the spatial filter/source mask (i.e., at any optical plane between the location of the filter/mask 420 and the image-plane/inspection surface/plane PL). EC distribution map 159 may represent a desired exposure condition to be approximately emulated at an image plane of the optical system or at a Fourier plane thereof. In such cases, conversion module 112 may optionally be employed to convert the received EC distribution map 159 into a desired TC distribution map 160 indicating a transmittance pattern which should be provided by the spatial filter to emulate the desired exposure condition. In the following, the operation of the classification module 110 and binary pattern module 130 are described enabling to approximate the desired exposure condition through binary spatial filter indicated by filter data 170.

The classification module 110 is configured and operable for receiving/retrieving EC distribution map 160 (or a TC distribution map 159) and categorizing values in this map 160 into a set of bin values (bin values are also referred to herein as classes or categories) and replacing each value in said map 160 with a corresponding value in the set of bin values to thereby generate a blobbed map indicative of the desired spatial filter to be obtained. The set of classes/bin values may be a predetermined set (independent of the EC map 160 to be processed), or alternatively the bin values, and possibly also the number of bins, are determined based on the EC distribution map 160 and/or TC distribution map 159. In some embodiments of the invention, the classification module 110 utilizes tolerance data 158, for processing the EC distribution map 160.

For example, the tolerance data 158 may include any one or more of the following: (i) transmittance tolerance data indicative of allowable variation between the transmission values of the blobs and the transmission/intensity values of corresponding regions in the EC distribution map 160 (or TC map 159); (ii) geometric tolerance data indicative of allowable variation in the geometric shapes of the blobs; and (iii) production tolerance data indicative of the production tolerances associated with the pattern generation module 200. In accordance with the tolerance data 158, the processing utility 102 may be configured and operable to modify any one or more of the shapes of the blobs, their respective transmission values and also the binary transmission patterns which may be subsequently used to substitute the blobs as described further below. Accordingly the processing utility 102, determines a design data 170 of a spatial filter having a binary pattern corresponding to the intensity distribution map 160 within tolerances provided by the tolerance data 158.

Specifically, in the present example, the classification module 110 may utilize the transmittance tolerance data to determine a set of transmission values (bin values) which can be used to substitute the transmission values in the intensity distribution map 160 (e.g., or in its corresponding TC map 159 as the case may be). Typically, the number of bin transmission values complies with at least one of the following: being less than a number of distinct transmission values in the intensity distribution map 160, and not exceeding 6 transmission values.

Thus the classification module 110 may utilize the tolerance data 158 to determine the set of classes/bin values and/or to determine association data (e.g., rules, lookup tables and the like) associating each intensity value/pixel of EC distribution map 160 with a certain bin value. In this regard it should be understood that associating a pixel in the EC distribution map 160 with a corresponding bin value may be performed by selecting the bin value which is closest to the pixel value according to any suitable distance function (being a linear function or other).

72.1. The blobbed map 162 is thus obtained by classifying and replacing the values of "pixels" in the EC distribution map 160 with bin values corresponding thereto. In this manner, pixels of the EC distribution map 160 are grouped to form blobs of adjacent pixels of the same bin-value (class), and thus a blobbed map 162 is formed.

In some embodiments of the invention, the classification module 110 may be configured and operable for providing blobbed map 162 in which the blob sizes are above a certain minimal size. For example, in accordance with the tolerance data 158 (e.g., geometric tolerance data), the blobs' sizes may be manipulated and modified by inflating/dilating or deflating too small or too large blobs (e.g., in an isotropic manner). In some cases, the transmission value (bin value) of such a modified blob may be replaced/exchanged by another bin value, such as to approximately maintain the total transmittance through the blob and to thereby improve the accuracy of the approximated emulated exposure condition obtained by the binary spatial filter. Also in accordance with the tolerance data 158 (e.g., geometric tolerance data), classification module 110 may be configured and operable to consolidate small blobs, when possible, with adjacent blobs to thereby form consolidated blobs with sizes above a certain minimal size.

Binary pattern module 130 is configured for processing the blobbed intensity map 162 formed by classification module 110 and generating a binary filter design (filter data 170) corresponding thereto and accordingly to the EC distribution map 160. Each blob in the blob map 162 is associated with a certain bin-value/class corresponding to a certain property of interest (typically, to the average transmittance/reflectance through the blob). Binary pattern module 130 is operable for replacing at least one blob of the blobbed map 162 with a corresponding binary pattern which has the similar value of that certain property (optimized binary transmission patterns having similar average transmissions).

It should be understood that according to certain embodiments of the invention, binary pattern module 130 utilizes a stock of binary patterns (reference data e.g., stored in memory 140), and is operable for replacing blobs in the blobbed map 162 by selecting suitable binary patterns from the stock. Alternatively or additionally, according to certain embodiments of the invention, the binary pattern module 130 is operable for generating binary patterns based on certain properties of the blob to be replaced. Thus, the binary patterns may be generated from scratch in accordance with the blob property (e.g., transmission value), or they can be generated by manipulating ready binary patterns which are stored in memory (e.g., 140). In the latter case, binary pattern module 130 may be configured and operable for utilizing tolerance data 158 (e.g., geometric tolerance and/or production tolerance data) to determine which binary transmission pattern is most suited for replacing a blob.

Figure 2B:
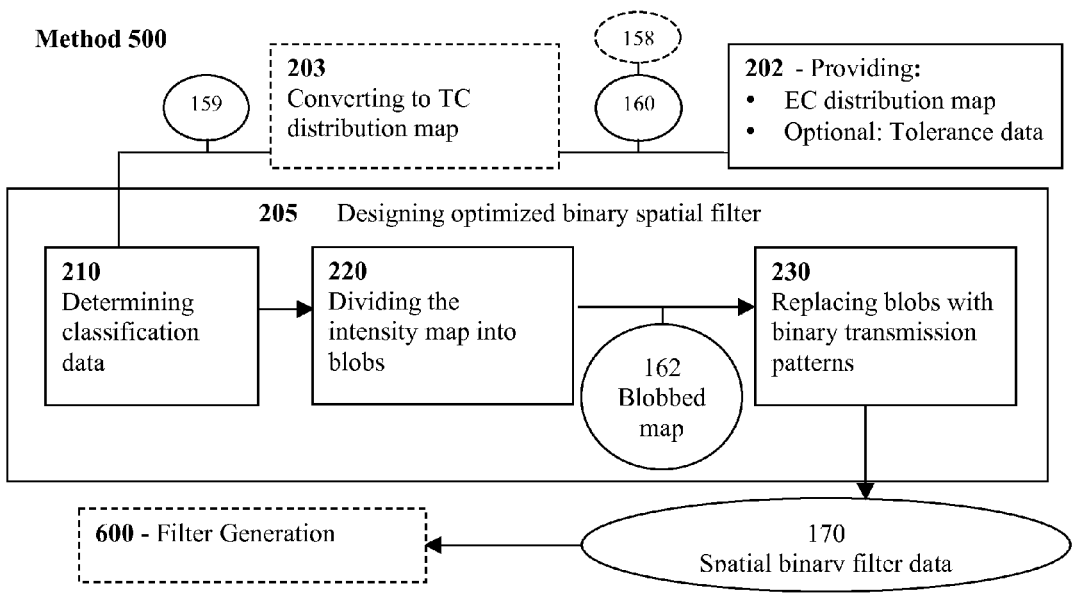

Turning now to FIG. 2B there is illustrated a flow chart 500 of an embodiment of a method for processing an EC distribution map 160 and generating data 170 indicative of an optimized binary mask. This method is an example of a possible operation of the binary filter design system 100 exemplified in FIGS. 1 and 2A. Illustrations exemplifying the possible operation and the results at various stages of this method are shown for example in FIGS. 3A-3G and are described together with the method steps of FIG. 2B.

In 202, an EC distribution map 160 is provided. Generally, the EC distribution map 160 is indicative of a desired distribution of a certain illumination/exposure property. For accurate patterning or aerial inspection, it is typically desirable to obtain an inspecting light (e.g., L2 of FIG. 1) in which the distribution of the certain illumination property, at a certain imaging/inspection plane/surface, corresponds to the EC distribution map 160. This EC distribution map 160 is processed to determine an optimized binary filter pattern 170 (steps 205). The filter pattern/data 170 is designed such that when light passing through this pattern at a first plane arrives at a certain second plane/surface (e.g., inspection plane on the aerial inspection system), it has intensity distribution resembling distribution of the certain illumination property comparable with the desired EC distribution 160 (e.g., approximating EC distribution in accordance with the predetermined tolerance data 158).

According to some embodiments of the invention, the first and second surfaces are located in different planes. In such embodiments, an additional procedure 203 may be employed (e.g., by conversion module 112 of FIG. 2A) for converting the EC distribution map 160 into a desired TC distribution map 159. This can be achieved by utilizing any algorithm capable of devising the distribution of an exposure property of interest within the light beam at one surface based on the distribution of a corresponding property at another surface (e.g., algorithms simulating/computing wavefront propagation of a light beam along an optical path between the two surfaces).

In some other embodiments, the received EC distribution map 160 may be identical to, or indicative of the desired TC distribution map 159 to be obtained/approximated by the optimized binary mask pattern indicated by filter data 170. For example, the EC distribution map 160 may correspond to a desired lateral EC distribution of the light beam at a certain plane/surface and the TC distribution map 159 indicative of a certain transmittance pattern to be implemented by a filter (e.g., located at the same plane/surface) for obtaining/approximating the desired lateral intensity distribution.

The TC distribution map 159 is generally indicative of a desired design of an aperture arrangement to be applied to the light for obtaining the desired exposure condition or intensity distribution (as indicated by EC distribution map 160). The TC distribution map 159 may be, for example, generated/provided in the form of a gray level square image of typically 101×101 or 201×201 pixels.

In the following, the processing to the EC distribution map 160 is considered for designing the binary filter and providing filter data 170 indicative thereof. It should be however noted that in some cases, the processing described below is actually carried out on the TC distribution map, specifically in cases where some pre-conversion is applied to the EC distribution map 160 to produce a TC distribution map 159 that is indicative of the desired transmittance/reflectance through the spatial filter.

The binary filter pattern/data 170 is determined based on the EC distribution map 160 typically via several stages including classification stage 210, association stage 220, and binary pattern design stage 230. In the classification stage and association stages, 210 and 220 (e.g., performed by classification module 110 of FIG. 2A), the EC distribution map 160 is processed to form a blobbed map 162. Then, in the binary pattern design stage 230 (e.g., performed by binary pattern module 130 of FIG. 2A), the blobs in the blobbed map 162 are replaced by suitable binary patterns allowing to approximately obtain the desired distribution of the certain illumination property as indicated by EC distribution map 160.

During the classification stage 210, the "colors" (i.e., values/transmittance values) in the EC distribution map 160 are classified and respectively associated with a smaller set of bins (i.e., category values). Optionally, classification data, including for example a set of rules or a lookup table (LUT), for classifying transmittance values into bins, is obtained.

As noted above, bin values may be a set of predetermined values. In some other embodiments, alternatively or additionally, the set of bin values (or some of them) may be determined based on the EC distribution map 160. The set of bin values may be designed to optimally associate pixels in the EC distribution map 160 with a small number of "colors"/bin-values. In some embodiments the set of bin values is selected for reducing/minimizing both the number of colors/bin values and a variance between the EC distribution map 160 and a blobbed map 162 obtained in a manner described below. Typically, a number of bin values obtained at this stage substantially does not exceed 6 values. In some embodiments, the set of possible bin values are provided/determined independently from the EC distribution map 160.

In the association stage 220, pixels in the EC distribution map 160 are replaced with the bin values which correspond thereto. The pixels' values may be replaced with the bin values for example based on LUT determined in the classification stage 210 or via classification rule. Such a classification rule may be predetermined, for example based on a certain distance function to measure the "distance" between the pixels and bins and categorizing a pixel according to the nearest bin closest thereto. A distance function may be a linear or non linear function which provides a measure for a distance between a bin value and a pixel value (e.g., normalized pixel value or not).

By replacing pixels in the EC distribution map 160, a blobbed map 162 is formed. For example, each blob has a single homogeneous transmission value. At this stage, several operations may be carried out in order to further optimize the design of the binary spatial filter. For example, if increased total transmission of the blobbed map is desired/required, then transmission through each of the blobs may be increased by the appropriate factor.

Optionally, during the classification and/or association stages, 210 and 220, the values of the pixels may be normalized. Typically, pixel values are normalized to the scale of the bin values. Normalization may be performed utilizing any suitable function (i.e., representing linear or non-linear relation between the original pixel value and the normalized one). Generally, pixel values and/or bin values may be either scalars or multi-dimensional values (e.g., vectors, RGB values). Accordingly, the normalization and the distance function are selected in accordance with the dimensions of the pixel and bin values. It should also be understood that a normalization operation/function may be seamlessly incorporated in the distance computation function.

Figure 3A:
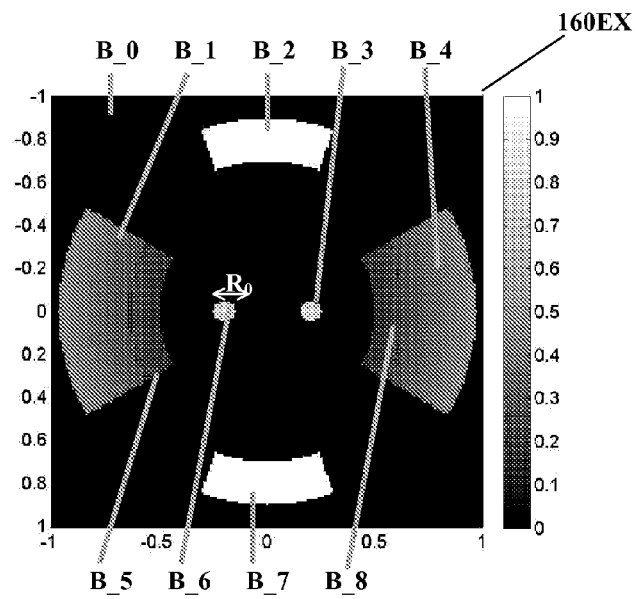
FIGS. 3A to 3G exemplify design of a binary spatial filter pattern by processing the input exposure condition distribution map using the method of FIGS. 2A and 2B.
Figure 3B:
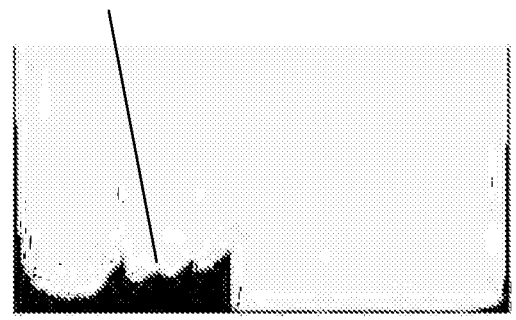

FIGS. 3A to 3G exemplify a pattern of a binary spatial filters obtained by applying the above described data processing method of the invention on an input EC distribution map. An example of the classification and blob creation stages 210 and 220 is illustrated by FIGS. 3A to 3D. An image 160EX exemplifying an EC distribution map 160 is shown in FIG. 3A. In this image, as in some embodiments of the invention, each pixel in the EC distribution map 160 is represented as a gray scale value between 0 and 255 (e.g., 8 bit value). A few bin-values (bins/classes/categories), to which the pixels of the TC distribution map 160EX are classified, are shown for example in FIG. 3C. The bin values are selected to cover a desired exposure condition of the EC distribution map 160 (e.g., to provide a desired transmittance/reflectance range, as indicated by the EC distribution map 160EX).

Figure 3C:
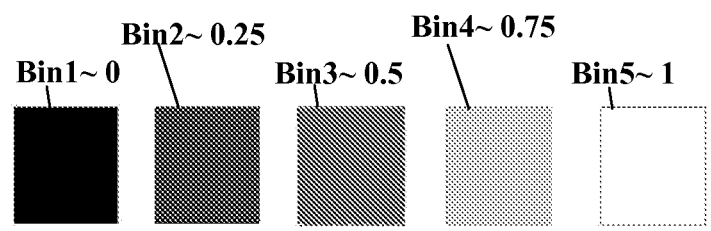

In the example of FIG. 3C, five predetermined bin values ranging from 0 (non-transmissive/reflective pixel) to 5 (fully-transmissive/reflective pixel) are used. The five bins Bin1 . . . Bin5 are respectively centered at 0, 0.25, 0.5, 0.75 and 1.

The set of bin-values, and possibly the bin-value number, are determined based on the transmittance distribution map 160E. To this end, various techniques may be used in the classification stage 210 (e.g., by classifier module 110) to determine the set of bin values. In a specific but not limiting example, during classification stage 210, a histogram 160HIST (illustrated in FIG. 3B) is processed (e.g., before or after normalization of pixel values). The histogram is indicative of the number of occurrences/frequency of various pixel values in the EC map 160EX. The histogram profile is divided into several histogram regions. Each region is classified during the classification stage 210 and associated with a certain bin-value. Bin values used for classifying each region are typically selected such as to reduce the variance/"distance" between the EC map 160 and a blobbed map to be produced in the next stage (220). Division of the histogram may also be based on the histograms profile. For example, considering the locations of major minima's and maxima's in the histogram profile and/or the sizes of areas bounded below the histogram line at different regions and/or the number of bins to be obtained, each histogram region is associated with a corresponding bin value which may be computed from the histogram region itself. A bin value can be computed by averaging the frequencies of different values in this region utilizing a certain weighting function.

As noted above, in the blob creation stage 220, a blobbed map 162 is generated by replacing pixels in the transmittance distribution map 160 with corresponding bin values (in accordance with classification data 161). It should be noted here that stages classifying and blob creation steps 210 and 220 may be performed sequentially: the pixels are classified and then replaced with the proper bin values, or alternatively these steps (classifying and replacing pixel values with bin values) may be performed concurrently.

The blobbed map obtained in stage 220 is formed as an image in which each pixel value is one of a few possible bin values. Since typically a small number of bins are used (typically no more than 10 and preferably not exceeding 6), then adjacent pixels are typically associated with the same bin value and thus blob regions are formed (each blob is associated with a certain bin value). Typically, for most aerial inspection applications, four or five bin values are sufficient to generate an adequate binary spatial filter which, when used, provides good identification of defective items with low rate of miss-identification (namely low rate of cases at which a defective pattern is not identified as such). The number of bin values or other data indicative of the tolerable variation between the pixels values in the EC distribution map 160 and corresponding bin values by which the pixels are replaced, may for example be provided in the tolerance data 158.

Figure 3D:
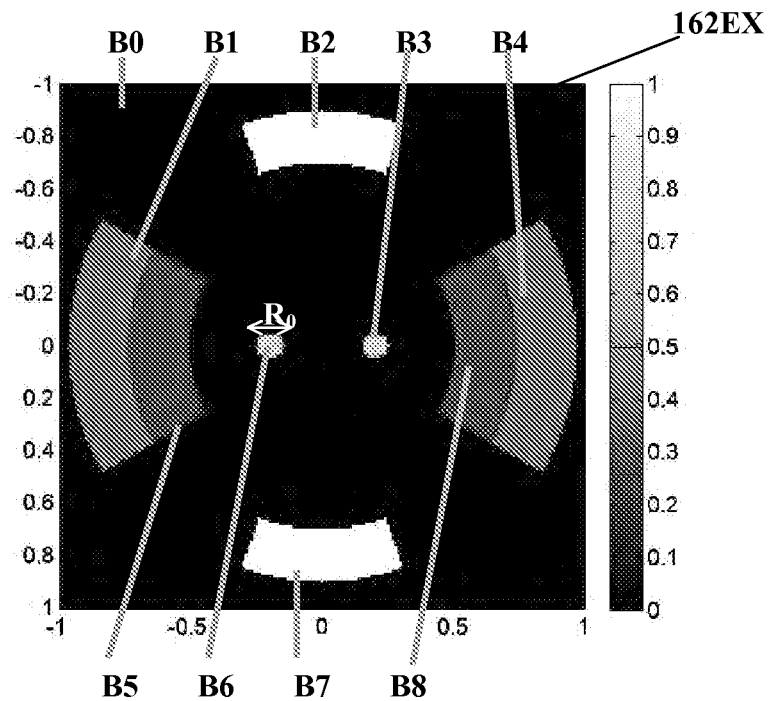

FIG. 3D shows an example of a blobbed map 162EX, formed by applying the above described classifying and blob creation stages 210 and 220 to the EC distribution map 160EX of FIG. 3A. Blobs B0 to B8 are depicted in the blobbed map 162EX. Each of the blobs B0 to B8 is associated with one bin value (from the set of bin values Bin1-Bin5 of FIG. 3C) indicating, in this example, transmittance through the blob. In FIG. 3D, blobs B0 is associated with bin value Bin1 of FIG. 3D, and accordingly blobs B5 and B8 are associated with Bin2, blobs B1 and B4 are associated with Bin3, blobs B3 and B6 are associated with Bin4 and, blobs B2 and B7 are associated with Bin5.

Thus, at the end of the blob creation stage 220, a relatively large number of values in the EC distribution map 160 is reduced to a few transmittance values in the blobbed map 162. Preferably, according to some embodiments of the invention, the total transmission through the blobs (e.g., B0 to B8) is maintained equal to the total transmittance through corresponding regions of the TC distribution map 160EX (e.g., B_0 to B_8 in FIG. 3A).

In stage 230, filter data/pattern 170 being a binary map/pattern of a binary source mask suited for use for aerial imaging, is obtained by replacing the blobs in the blobbed map 162 with suitable binary patterns. As noted above, each blob in the blobbed map 162 is associated with a certain bin value which is, in turn, associated with a certain optical property such as an average transmittance, reflectance or luminance. One or more blobs of the blobbed map 162 are replaced by suitable binary patterns.

A binary pattern may be considered as being suitable to replace a blob, if it has either an average/specific value of the certain optical property that is substantially similar to the bin value of the blob, or alternatively or additionally, if the total value of that certain optical property (e.g., the total transmittance) is maintained while replacing the blob with the binary pattern. To this end, the tolerance data 158 may include data indicative of the allowable differences in between the transmission of the blobbed map 162 and the transmission of the EC map 160.

Alternatively or additionally, a binary pattern may be considered as being suitable to replace a blob, if it can modify (inflate or deflate) the size/region of the blob by a few percentages, such that when this binary pattern is used, the total value of that certain optical property is substantially maintained. For most imaging/inspection applications, a blob region can be inflated or deflated by up to 20 percentages (preferably by no more than 10 percentages) without substantially impairing the accuracy of inspection. Optionally, tolerance data 158 includes geometric tolerance data indicative of allowable variations in the blobs' sizes and possibly also production tolerances indicative of the variability and minimal feature size which can be implemented when generating the binary spatial filter.

In stage 230 (blob replacement by binary pattern), the following techniques may be used in order to optimize the resultant binary source mask 170:

Blobs associated with the highest energy bin(s) may be represented by "open polygons" (a polygon being a function describing the contour of a blob). Then isotropic inflation/dilation of such blobs may be applied to increase the energy/total-transmission of such blobs.

Blobs associated with the low energy bin, may be replaced by smaller regions of higher transmission (e.g., with fully transmitting regions such as "holes" or "perforations"). The size (area) of the regions should preferably be computed to give the required transmission. Moreover, a minimal size ("hole" size) of such blobs may be required to satisfy optical constraints (e.g., diffraction) and/or mechanical constraints (e.g., production tolerances) which might be imposed by the technique used for implementing the binary source mask in accordance with data 170 (e.g., perforated foil, CUG or other)

Some small blobs of intermediate bin-values (e.g., partially transmitting blobs) may include only a few "holes"/transmission regions when replaced with their corresponding binary pattern. Then, such small blobs may be instead replaced by a single perforation/hole/transmitting region. The partial transmission of such blobs may be compensated for by an isotropic dilation of the blob.

Other optimizations of the binary source mask may include: (a) randomizing the positions of "holes"/transmitting regions, e.g., this may reduce aliasing and interference effects; (b) symmetrizing transmission-regions of symmetrical blobs; (c) confirming and adapting blob shapes such that blobs and/or transmission-regions thereon do not intersect and prune/replace intersecting/touching regions.

The arrangement and configuration of transmitting regions on the binary source mask data 170 may be further processed in order to determine other alternative configurations which minimize a number of transmission-regions. This might save design time, manufacturing time and costs in implementing the binary source mask.

Figure 3E:
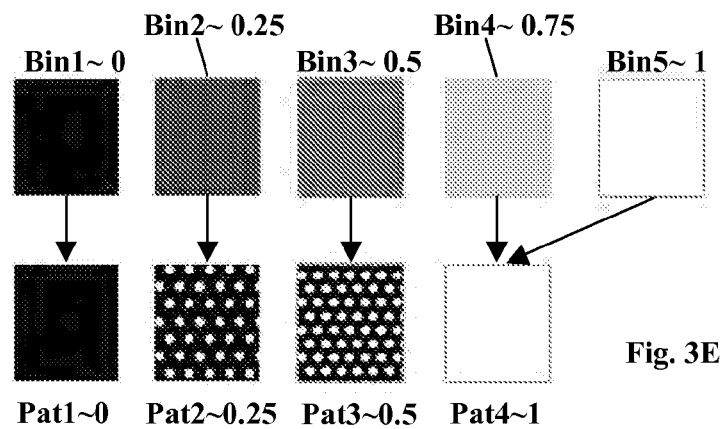
Figure 3F:
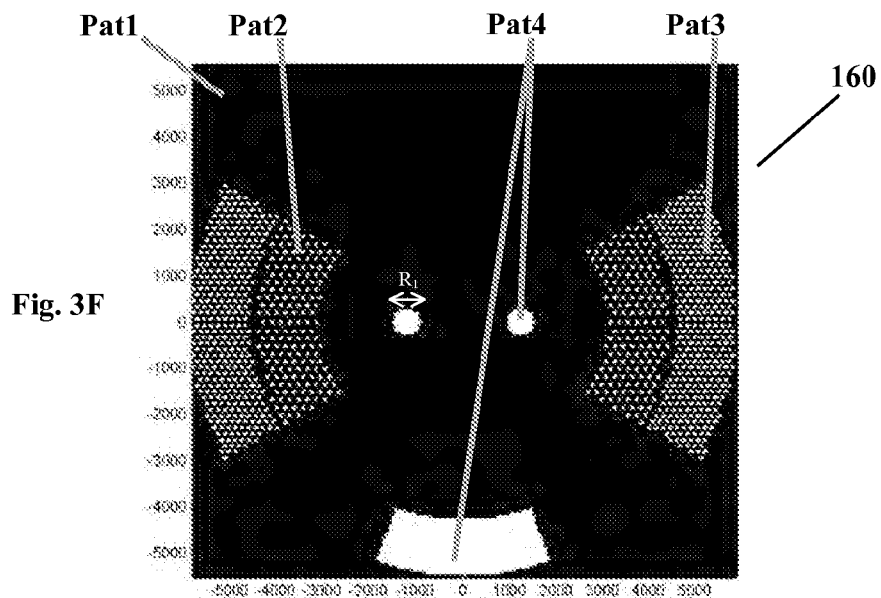
Figure 3G:
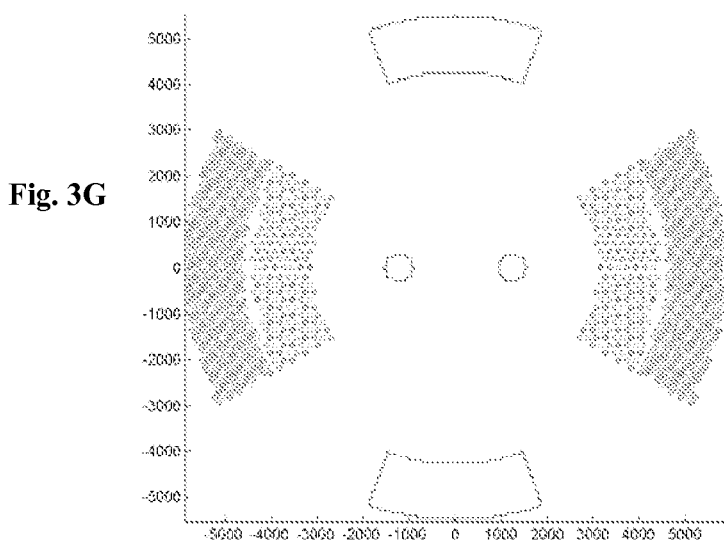

FIG. 3F shows an example of a filter data indicative of a binary spatial filter/mask 170EX that corresponds to the exemplified transmittance distribution map 160EX. The binary mask 170EX is obtained by utilizing replacement of blobs in the blobbed map 162EX (step 230) with the binary patterns Pat1 to Pat4 shown in FIG. 3E. A contour plot 170CNTR corresponding to the binary source mask 170EX is shown in FIG. 3G. Contour plot 170CNTR is an example of an operative map to be transferred to a cutting/pattern generation module for creating a mask, for example a perforated foil mask, corresponding to the mask 170EX.

The operation of the blob replacement stage 230 can be better understood by considering the example shown in FIGS. 3E and 3F. Referring to FIG. 3E, bin values Bin1 to Bin5 are illustrated with association to corresponding binary patterns Pat1 to Pat4. The binary patterns Pat1 to Pat4 are formed as spaced apart regions of two transmittance values. In this example, binary patterns Pat1 to Pat4 are marked with black color for representing substantially non transmissive regions (opaque regions) and white color for representing substantially fully transmissive regions. Indeed, the average transmittance values of patterns Pat1, Pat2, Pat3 and Pat4 are approximately of the bin values Bin1, Bin2, Bin3, and Bin5, respectively. Accordingly, when these patterns are used to replace blobs corresponding to respectively bin values Bin1, Bin2, Bin3, and Bin5, the same average transmittance is obtained, and actually the same total transmittance of each blob is maintained. To this end, patterns Pat1, Pat2, Pat3 and Pat4 may be considered substantially equivalent to blobs with bin values Bin1, Bin2, Bin3, and Bin5 respectively.

However, as can also be seen from FIG. 3E, a binary pattern with a certain value of the certain optical property may also serve for replacing blobs with different bin values (e.g., that have different average value of said certain optical property). For example, blobs B3 and B6, which are associated with bin value Bin4, are replaced in the present example by pattern Pat4 which has a different average transmittance then bin value Bin4. The average transmittance value of Bin4 is 0.75, while the average transmittance of Pat4 is 1 (fully transmissive). This forms a discrepancy between a bin value of a blob and the average value of the certain optical property of the binary patterns used for replacing the blob. According to the invention, such discrepancy can be compensated by modifying the extent of the blob region, in which the pattern is introduced, such that the total value of the optical property is maintained (e.g., the total transmittance through the blob is maintained by inflating or deflating the blob).

In the present example, the total transmittance $T_0$ through blob B6 is proportional to its corresponding bin value Bin4 multiplied by its area $\pi R_0^2$ ($R_0$ being the characteristic radius of the blob B6). The total transmittance $T_1$, obtained after replacing the blob with binary pattern Pat4, equals to the area of the replaced region $\pi R_1^2$ times the average transmittance of pattern Pat4, which equals in this example to Bin5. The radius $R_1$ is a new characteristic radius of a region to which pattern Pat4 was inserted. Thus, in order to maintain the same total transmittance, namely in order to obtain a condition that $T_0=T_1$, the characteristic size $R_1$ of the region to which Pat4 is placed to replace blob B6 should be $R_1=R_0*Sqrt(Bin4/Bin5)$, where Sqrt represents the square-root function. Thus, the characteristic size/radius of the replaced region is inflated or deflated with respect to the original characteristic size/radius of the blob. In this example, Bin4 corresponds to a smaller transmission than Bin5, and thus the new characteristic size $R_1$ of blob B6 is smaller than its original size $R_0$.

It should be noted that the operation of the blob replacement stage 230 may utilize readymade binary patterns of predetermined optical properties and possibly predetermined characteristic feature sizes. Alternatively or additionally, during the blob replacement stage 230, binary patterns, suitable for replacing certain blobs, may be created (obtained by suitable processing) on-the-fly in accordance with the desired optical property of the blob (e.g., 70% transmission) and in accordance with the characteristic properties of the two regions from which the spatial binary filter/mask is actually created (e.g., fully-transmissive and fully opaque regions such as in a pattered foil mask).

For example, binary patterns, such as those shown in FIG. 3E, may be formed on-the-fly by embedding regions of predetermined shape (e.g., circular regions) and of a certain value of the optical property of interest (e.g., fully transmissive regions) within regions of a certain other values of the optical property of interest (e.g., opaque regions). The size and density of the embedded regions are selected (e.g., obtained automatically) in accordance with the desired value of the optical property of interest with which the pattern should comply (e.g., 70% transmission) and possibly also in accordance with a desired feature size.

It should be noted that, typically, utilizing binary patterns with too small and/or too dense features (e.g., features below a few tens of microns) may introduce diffraction and/or interference effects. In many cases, this should be avoided in order not to impair aerial inspection/patterning. On the other hand, replacing blobs, or regions of the original transmittance distribution map 160, with binary patterns with too large features (e.g., features in the order of few millimeters and larger) may introduce artifacts to the aerial inspection and impair its accuracy. Accordingly, the binary patterns used in the aerial inspection typically include features of size in the order of about 100 microns or a few hundreds of microns.

As a result of the technique of the present invention, as described above with reference to binary filter design system 100 and to the above-described method of designing a spatial binary mask, the suitable filters for use in aerial inspection or patterning system can be implemented as optimized spatial binary filters formed with spaced apart arrangement of two types of regions of different optical properties. In many embodiments of the present invention, the two types of regions correspondingly have two distinct levels of transmittance and/or two distinct levels of reflectance. This is advantageous over other techniques at least because it allows usage of simple binary filters instead of multi-value filters/masks which are harder to implement (specifically when on-the-fly implementation of such filters is being considered). One type of such binary spatial filter can be implemented utilizing for example, perforated/patterned foil to define a spaced apart arrangement of fully-opaque and fully-transmissive regions, i.e., an arrangement of spaced-apart apertures/perforations in a non-transparent substrate (foil).

Non-binary (multi-valued) mask/aperture designs (e.g., TC distribution maps), are typically difficult to implement and require techniques such as CUG. The mask design technique of the invention allows for reducing the mask requirements to binary mask designs, which can be implemented on demand more easily. This is obtained without substantially impairing the performance of aerial inspection/patterning systems utilizing binary spatial filters.

As described above, a dynamic (i.e., transient) binary spatial filter may be implemented by utilizing a spatial light modulation technique of the present invention, according to which the filter implementation system (22 in FIG. 1) is capable of on-the-fly generation of transient binary spatial filters. According to this technique, an optimized binary spatial filter is formed by printing, on an optical surface, a fluid pattern corresponding to the desired pattern of the binary spatial filter. The optical surface serves as a filter carrier module (300 in FIG. 1). The optical properties of the optical surface, the ambient optical medium interfacing therewith and the printed fluid are selected such as to create an arrangement of spaced-apart regions of two different total internal reflection (TIR) angles. Patterning/structuring light beam is then achieved by directing input light onto the optical surface with an angle between the TIR angles of the pattern, such that portions of this light are reflected (due to TIR condition) from the surface, while other portions of the light pass the surface without being reflected therefrom and preferably without being absorbed thereby. At least one of the reflected/transmitted light portions forms a structured light in accordance with the desired binary spatial filter pattern.

Figure 4A:
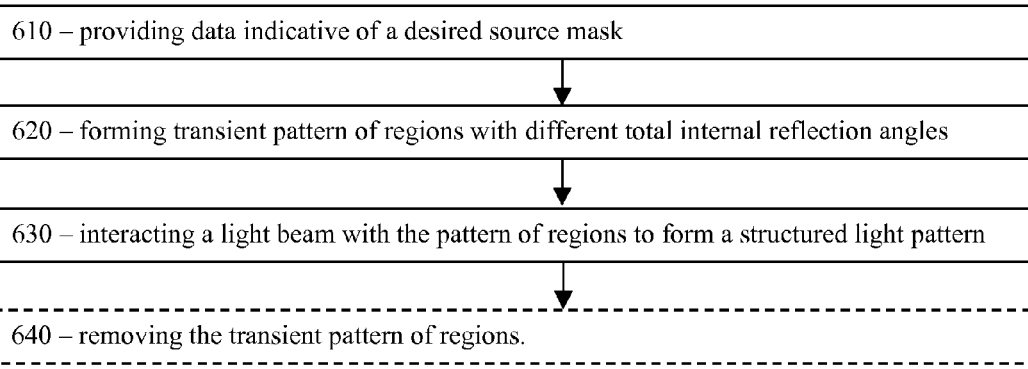
FIGS. 4A and 4B show schematically an implementation method and system according to the present invention for dynamic implementation/generation of binary filters (source masks).

An example of the above-described technique of the present invention for implementing dynamic binary spatial filters (suitable for use in aerial inspection) will now be described with reference to FIGS. 4A-4F. FIG. 4A is a flow chart 600 of a method for implementing/generating a transient binary spatial filter in the form of an arrangement of spaced apart regions with two different optical properties. Specifically, this method is adapted for generating reflective and/or transmissive spatial filters from which a certain light pattern is respectively reflected and/or transmitted.

Initially, filter data indicative of a desired binary spatial filter (source mask) is provided (step 610). The filter data is then utilized for forming a transient pattern of regions of different total internal reflection angles (step 620). Then, a light pattern (structured light) can be created corresponding to the desired source mask (step 630). This is achieved by interaction of an input light beam with the pattern of regions to cause reflection of a structured light pattern from said pattern of regions.

The desired source mask may be in the form of a binary pattern corresponding, for example, to a two dimensional arrangement of spaced apart regions of relatively high and low light intensity. Such a two dimensional arrangement may correspond to a desired intensity profile of light at a certain plane in the optical path of light propagation. According to certain embodiments of the invention, the desired source mask is obtained in accordance with the method described above with reference to FIG. 2B (e.g., by filter design system 100 of FIG. 2A).

In step 620, the desired binary spatial filter is implemented as a pattern of different total internal reflection angles. This is achieved by deployment of a liquid pattern on an optical surface, such that a certain total internal reflection angle is formed at regions at which the liquid interfaces the surface, which is different from a certain other total internal reflection angle in surface-regions/spaces between the liquid containing regions (e.g., at which the surface interfaces with ambient surroundings). This actually forms a pattern of reflection (e.g., a binary pattern) for light interacting with the optical surface in an angle between two total internal reflection angles. The technique of the invention may also be used to obtain a binary pattern of transmission (for example utilizing light guiding elements as described further below).

The optical surface is generally an interface between an optical medium (e.g., optical element) having a certain refraction index N interfacing an ambient environment/medium of refraction index $N_1$. A pattern of liquid with refraction index $N_2$ is formed on the surface. A first critical (total internal reflection) angle $\Theta_1$ of the pattern of different total internal reflection angles is associated with the interface between the optical surface and the ambient environment and equals $\Theta_1 = \arcsin(N_1/N)$.

According to some embodiments of the invention, the liquid pattern is formed on the surface from the side of the ambient medium, while the light is directed to interact with the other side of this surface. In these embodiments, the second total internal reflection angle $\Theta_2$ of the pattern of different total internal reflection angles is associated with the interface between the optical medium and the liquid and equals $\Theta_2 = \arcsin(N_2/N)$, different from the first total internal reflection angle $\Theta_1$.

According to some other embodiments of the invention, the liquid pattern is formed on the surface from the side of the optical medium, onto which light is directed to interact with the surface. In these embodiments, the second critical total internal reflection angle $\Theta_2$ is associated with an interface between the liquid and the ambient environment/medium and equals $\Theta_2 = \arcsin(N_2/N_1)$. Possibly, in such embodiments, the ambient medium is solid and the optical medium may be liquid.

In step 630, an input light beam of substantially collimated light rays is directed to impinge on the optical surface with an angle $\Theta$ that is between the first and second critical total internal reflection angles $\Theta_1$ and $\Theta_2$. Some of the light rays (e.g., those impinging on regions of the surface interfacing the liquid) traverse the interface without being substantially reflected therefrom. Other light rays (e.g., those impinging on regions of the surface interfacing the ambient environment) undergo total internal reflection when interacting with the surface thus creating reflected structured light corresponding to a binary pattern of reflection/transmission, indicative of the liquid pattern deployed on the surface (i.e., being the negative of that liquid pattern).

As noted above, this technique allows implementation of transient spatial-filters/masks of optical transmission and/or reflection. To this end, the term transient should be recognized with the ability to clear the spatial-filter implemented in step 620 and possibly replace it by another spatial-filter on demand.

Optionally, in step 640, the transient pattern of regions of different total internal reflection angles is removed by clearing the liquid from the optical surface. Then, another transient pattern of regions corresponding to another optimized binary spatial filter and other structured light pattern can be formed on the optical surface by repeating steps 610 and 620 described above. Removing/clearing the transient pattern can be performed for example by heating the optical surface for evaporating the liquid deployed thereon, and/or wiping or blowing the liquid from the surface, and/or changing affinity of the optical surface, and/or any combination of these techniques.

Figure 4B:
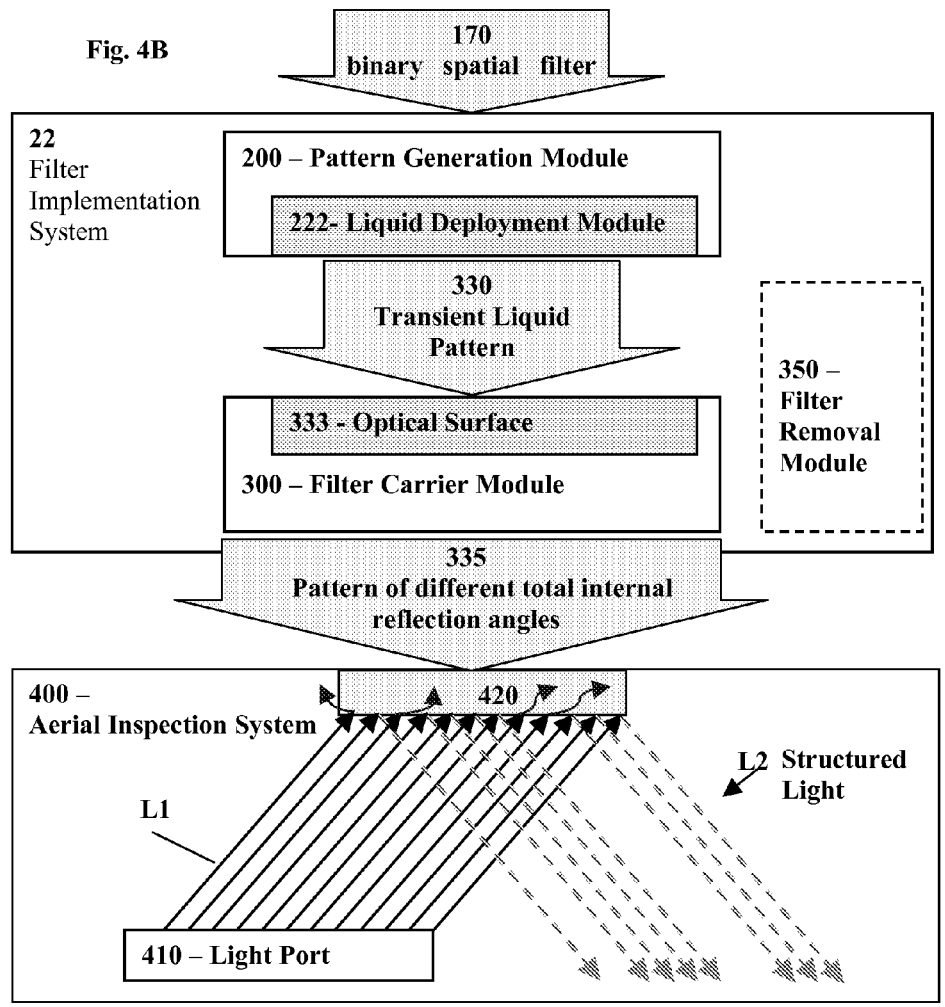

Reference is made to FIG. 4B illustrating more specifically, in a block diagram, an example of a filter implementation system 22 operative in accordance with the above described flow chart 600 and suitable for use in the system 10 of FIG. 1. Similarly to system 22 shown in FIG. 1, also here the mask implementation system 22 includes a mask pattern generation module 200 and a filter carrier module 300. Additionally, and optionally, filter implementation system 22 may also include filter removal module 350 configured and operable to clear an implemented filter/mask from the filter carrier module 300. This can be achieved utilizing any suitable technique as described above.

In this example, the filter carrier module 300 includes an optical element 333 of a certain refraction index N having an outer surface interfacing an ambient surroundings/environment with refraction index $N_1$. Also, in this example, the pattern generation module 200 is a liquid deployment module 222 which is configured and operable for receiving filter data indicative of a binary spatial filter, e.g., an optimized binary mask data (i.e., filter data/pattern) 170 obtained as described above, and deploying liquid on the optical surface of element 333 to form thereon a transient liquid pattern 330 corresponding to the received filter data.

The liquid deployment module 222 is typically adapted for deployment of suitable pattern of liquid with desired refraction index $N_2$. Liquid deployment module 222 is configured to operate in accordance with the above described method steps 610 and 620 to create, on the optical surface, a desired pattern 335 of regions of different total reflection angles. To this end, pattern 335 of regions of different total reflection angles implements an optical mask 420 which can be used for creation of structured light.

It should be noted that liquid deployment module 222 may be implemented as a type of printer module similar to a jet printing unit. For example, the liquid deployment module 222 may be operable to inject, onto the optical surface, droplets of a selected liquid with refraction index $N_2$. Typically, the liquid deployment module 222 and the liquid used are configured in accordance with one another to enable liquid patterns with a certain desired characteristic minimal feature size. This can be achieved for example by configuring the printer unit to dispose a droplet of a certain minimal size. This is in order to control and/or reduce or prevent interference and/or diffraction to affect the structure of light interacting with (reflected/transmitted) the liquid pattern carrying surface.

As further shown in FIG. 4B, an aerial inspection system 400 (constituting a patterning system) can be operated in accordance with the above described method (flow chart 600) and generating structured light L2 by utilizing the liquid deployment module 222 and the optical surface 333 described above. Similarly to the patterning/inspection technique described above in FIG. 1, also here the system 400 includes a light port 410 projecting collimated light beam (e.g., in the UV-DUV regimes) onto the spatial filter 420. Here, the spatial filter 420 is a spatial light modulator implemented by utilizing an arrangement of spaced apart regions of different internal reflection properties.

Indeed, for aerial inspection or other patterning systems, a binary pattern, formed by two types of regions of different internal reflections, may be used. It should be recognized that utilizing the above described binary filter design system 100 and method exemplified by flow chart 500, such a binary pattern can be used for implementing various types of inspection/patterning filters corresponding to binary and non-binary intensity maps.

It should, however, be understood that the arrangement of spaced apart regions of different internal reflection properties can be formed, according to the invention, with more than two types of different internal reflection regions. Accordingly, such an arrangement may be used for generating a non binary filter with several different transmission levels (several "gray levels"). This can be achieved for example by employing the system 22 and the method exemplified by flow chart 600 described above, with more than one liquid. For example, system 22 and the liquid deployment module 222 may be configured to utilize two liquids having two different refraction indices N2 and N3 and respectively associated with two different internal reflection angles $\Theta_2=\arcsin(N_2/N)$ and $\Theta_3=\arcsin(N_3/N)$. The system 22 may then be configured to receive also non-binary filter data (with 3 "gray" levels) and to print a pattern of three different internal reflection properties.

Spatial modulation of light utilizing such a pattern of multiple region types of different internal reflection properties can then be formed for example utilizing a single input light beam and relying on different transmittance/reflectance from the different region types. Alternatively or additionally, multiple light-ports (e.g., such as 410) with different properties, may be placed with different angular orientation with respect to the optical surface 333 (or using differently oriented light guiding units), for example a first light port 410 projecting light beam L1 at an angle between $\Theta$ and $\Theta_1$ and a second light port (not shown) projecting light beam (not shown) at an angle between $\Theta$ and $\Theta_2$. For example, one of the light beams (e.g., L1) would then be reflected by surface regions free of one of the liquids (i.e., that do not interface a certain one of the liquids), and the other light beam would be reflected only from surface regions that do not interface any one of the two liquids.

Reference is now made to FIGS. 4C to 4H schematically illustrating several different configurations of spatial filter implementation and corresponding configurations of the filter carrier module 330 of FIG. 4B with an optical spatial binary filter 420 thereon. Different implementations of transient liquid pattern 330 on an optical surface 333 of the filter carrier module 330 are also illustrated being adapted for structuring a light beam reflected from and/or transmitted through the optical surface 333.

In these examples, the filter carrier module 330 includes an optical medium with refraction index N having an optical surface interfacing an ambient medium with refraction index $N_1$. A transient liquid pattern 330 of liquid with refraction index $N_2$ is deployed on the surface from one side thereof (e.g., by mask pattern generation module which is not shown). Collimated light beam L1 is directed onto the surface with a certain incident angle $\Theta$ that is selected as described above such that certain rays of the light beam undergo total internal reflection when interacting with the surface.

Figure 4C:
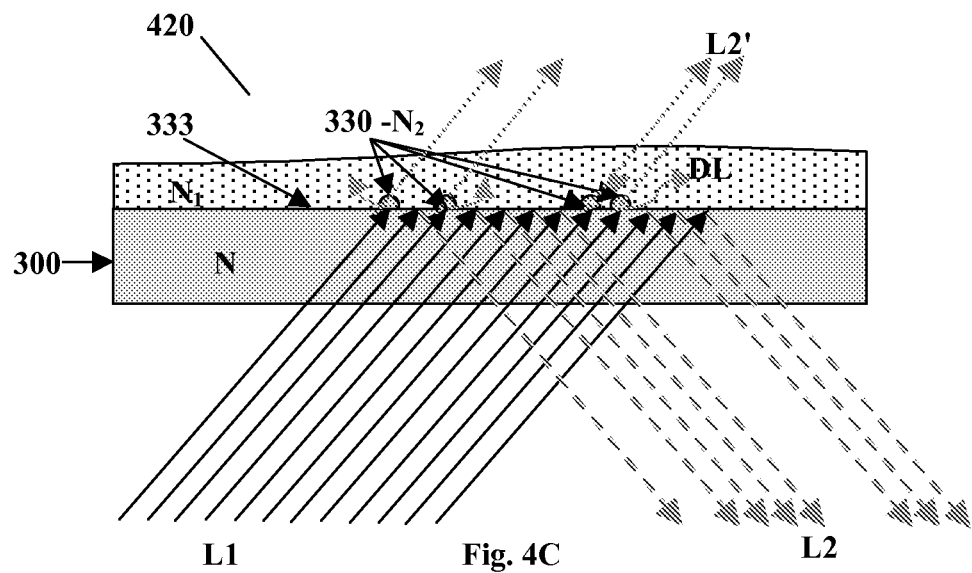
Figure 4D:
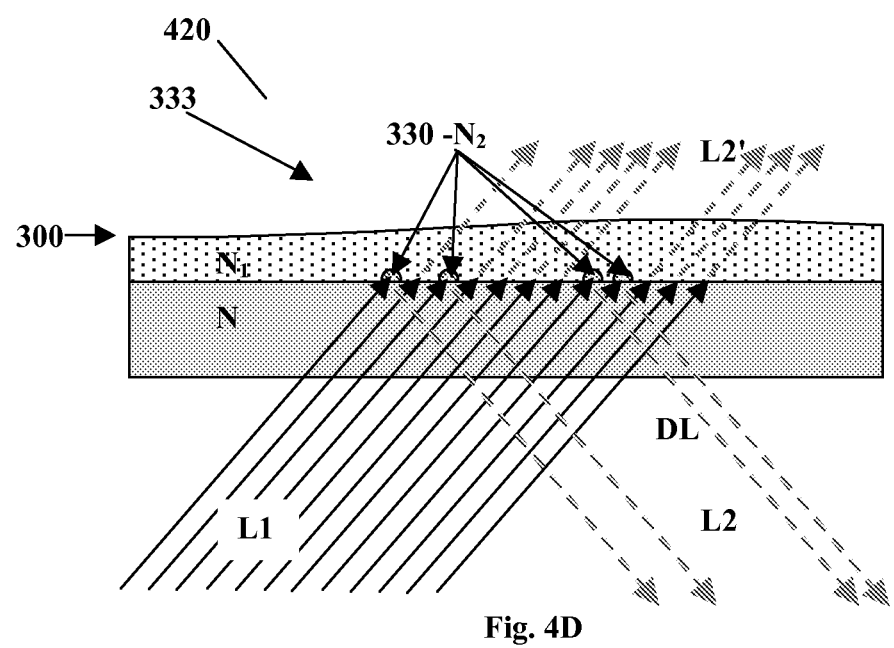

FIGS. 4C and 4D illustrate embodiments of the invention in which the light beam L1 is directed towards an optical surface of the filter carrier module 333 from its one side (the side of the optical medium with refraction index N), while the liquid pattern 330 is formed on its other side. In the example of FIG. 4C, refractive index $N_2$ of the liquid is greater than that of the ambient surroundings $N_1$. The collimated light rays L1 impinge on the surface and traverse the liquid containing regions 330 while undergoing total internal reflection from the surface regions that do not interface the liquid. In this example, a substantially accurate light pattern (structured light) L2 is formed by light rays reflected from the surface regions free of liquid. Light rays L2' that are transmitted through the liquid carrying surface regions may be diffused to some extent (e.g., due to the surface tension shaping the liquid droplets). Diffused light portions DL are also illustrated in the figure.

In this example, the optical surface may be formed of materials such as glass, PMMA and other optical materials (e.g., with $N\cong1.5$). The ambient surroundings of the surface may be vacuum or air (e.g., with $N_1\cong1$), and the liquid may be water (e.g., with $N_2\cong1.33$). Accordingly, a first critical total internal reflection angle $\Theta_1$ between the optical surface and the environment is $\Theta_1\cong\arcsin(1/1.5)\cong42$ deg, and a second critical total internal reflection angle $\Theta_2$ between the optical surface and the liquid is $\Theta_2\cong\arcsin(1/1.33)\cong49$ deg. In this case, collimated light beam may be structured by interacting with the optical surface at an angle $\Theta$ that is substantially equal to or slightly above $\Theta\geq42$ deg.

FIG. 4D illustrates another example in which the refractive index $N_2$ of the liquid is smaller than that of the ambient surroundings $N_1$. Collimated light rays L1, impinging on the surface with appropriate angle $\Theta$ of incidence, are reflected from the liquid pattern due to total internal reflection, while traversing surface regions interfacing the ambient surroundings. Here, substantially less or no light is diffused during interaction with the optical surface 333 and the liquid pattern 330.

As a result of the relation between the refractive index N of the optical medium from which the light propagates to the optical surface 333 and the refractive indices $N_1$ and $N_2$ of the liquid and ambient surroundings, neither the reflected light beam L2 nor the transmitted light L2' is refracted while interacting with curved surfaces of the liquid which do not interface the optical surface 333. Accordingly, in this example, reflected light L2 as well as transmitted light L2' are both structured accurately due to interaction with the liquid pattern 330. The reflected light L2 and the transmitted light L2' form complementary light structures each of which may be used for aerial inspection/patterning purposes.

Figure 4E:
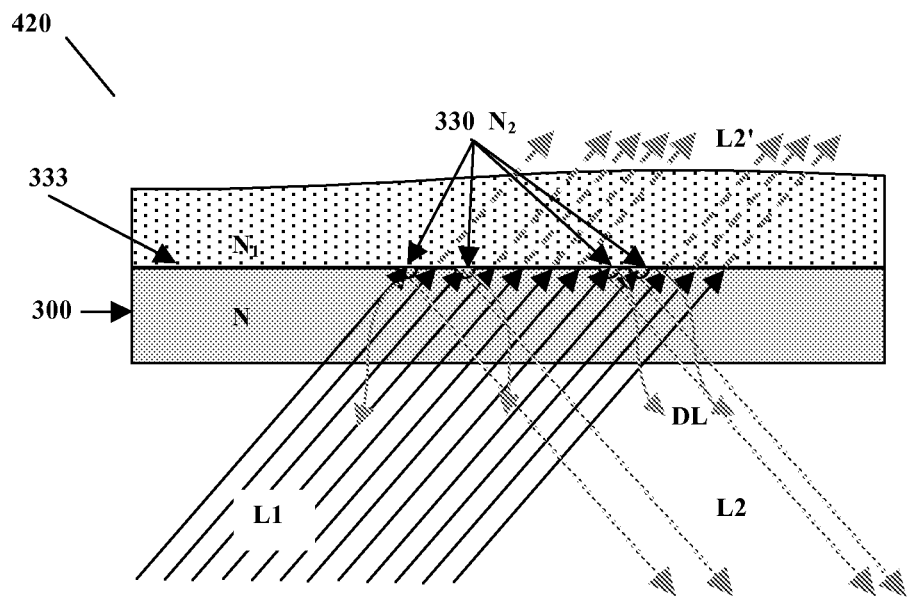
Figure 4F:
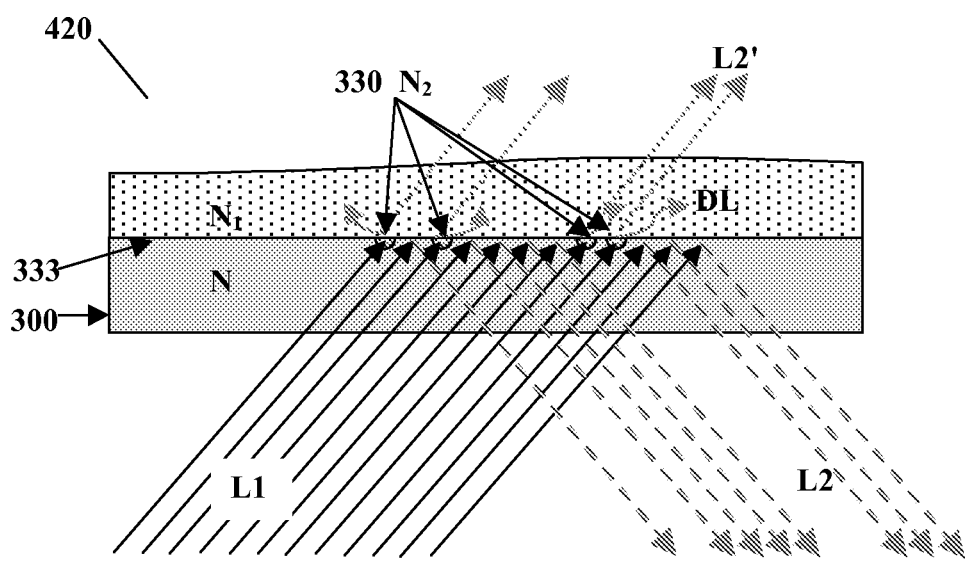

FIGS. 4E and 4F illustrate embodiments of the invention in which input light L1 is directed towards an optical surface 333 from the same side at which the liquid pattern 330 is formed. The first total internal reflection angle $\Theta_1$ corresponds to the interface between the optical medium of the surface (N) and the ambient medium and the second total internal reflection angle $\Theta_2$ corresponds to the interface between the liquid ($N_2$) and the ambient medium, and these angles are respectively $\Theta_1\cong\arcsin(N/N_1)$ and $\Theta_2\cong\arcsin(N_2/N_1)$.

The embodiment of FIG. 4E is an example of a transmissive formation of an optical binary spatial filter 420. The refractive indices N, $N_1$ and $N_2$ are selected such that $\Theta_1$ is greater than $\Theta_2$. Light beam L1 interacting with the optical surface 333 at an angle $\Theta$ satisfying a condition that $\Theta_2<\Theta<\Theta_1$ traverses the optical surface at interface regions between the optical medium (N) and the ambient medium ($N_1$), without undergoing total internal reflection. This forms the transmitted structured light L2' at the other side of the optical surface. Structured light L2' is almost not diffused during interaction with the liquid pattern inter alia because it had not interacted with the "curved" surfaces of the liquid.

The embodiment of FIG. 4F is an example of a reflective formation of an optical mask 420 according to the invention. The refractive indices N, $N_1$ and $N_2$ are selected such that $\Theta_1$ is smaller than $\Theta_2$. Light beam L1 interacting with the optical surface 333 at an angle $\Theta$ satisfying a condition that $\Theta_1<\Theta<\Theta_2$ is reflected from the optical surface at interface regions between the optical medium (N) and the ambient medium (N$_1$). This forms the reflected structured light beam L2 at the same side of the optical surface. Here, the structured light beam L2 substantially did not interact with the liquid and it is thus substantially not diffused.

FIGS. 4G and 4H show schematically, in a self explanatory manner, a filter carrier module 300 according to another embodiment of the invention utilizing a light guiding member LG. In this example, the light guiding member LG is configured for implementing an optical mask 420 of a transmissive type. The filter carrier module 300 and a light propagation scheme therethrough is illustrated in FIG. 4G. The general principles, configuration and operation of the filter carrier module 300 in this embodiment are similar to that described above with respect to FIG. 4C and will therefore not be repeated here.

In this embodiment, a light guiding member LG (e.g., including an optical prism unit) is utilized to receive an input light beam L1 through a light port 410 and to output light beam L2 through its output port 450. In this example, the input port 410 and output port 450 are facets of the guiding member. The light guiding member LG is optically configured to direct the light beam L1 to interact with the optical surface 333 of the filter carrier module 300 at an appropriate angle Θ and to collect the reflected light beam and direct it to output port 450. In this example, a surface of the light guiding member LG is configured as the optical surface 333 of the filter carrier module 300.

As indicated above, the present invention also provides a semi-/pseudo-dynamic pattern generation module capable of utilizing a stack of multiple (two or more) sigma wheels arranged along the direction of light propagation in between a light port (410 in FIG. 1) and an inspection plane PL. Each of the wheels may be configured for carrying several static filters/masks where the overall masking/filtering is formed by the accumulated effect of the selected combination of masks in all sigma wheels. Such a semi dynamic pattern generation module is adapted for receiving the desired filter design (e.g., optimized binary filter data obtained by the present invention as described above) and for switching/rotating the multiple sigma wheels to locate the most suited combination of static filters which best fits or approximates the desired filter design (e.g., within the acceptable tolerances as indicated by the tolerance data 158 of FIG. 1).

Figure 5B:
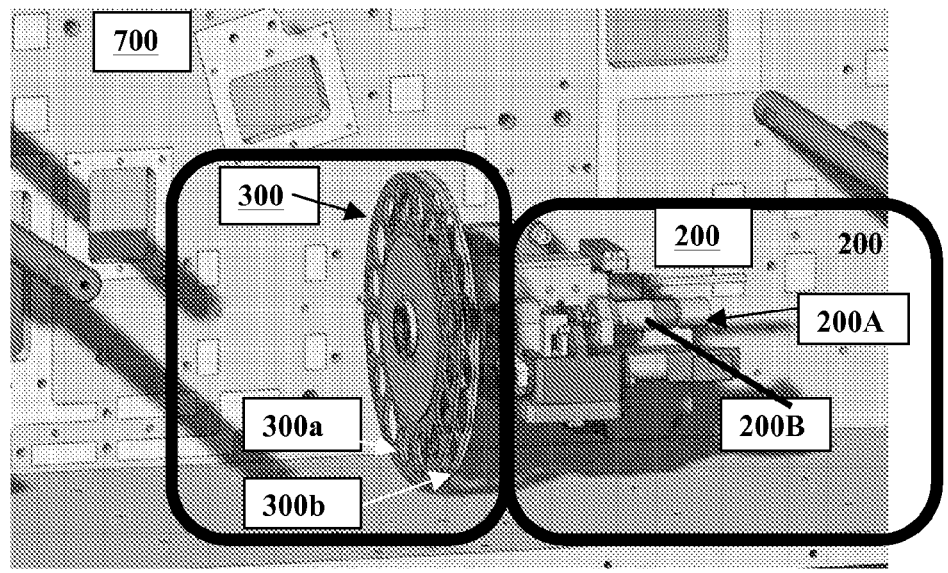
Figure 5C:
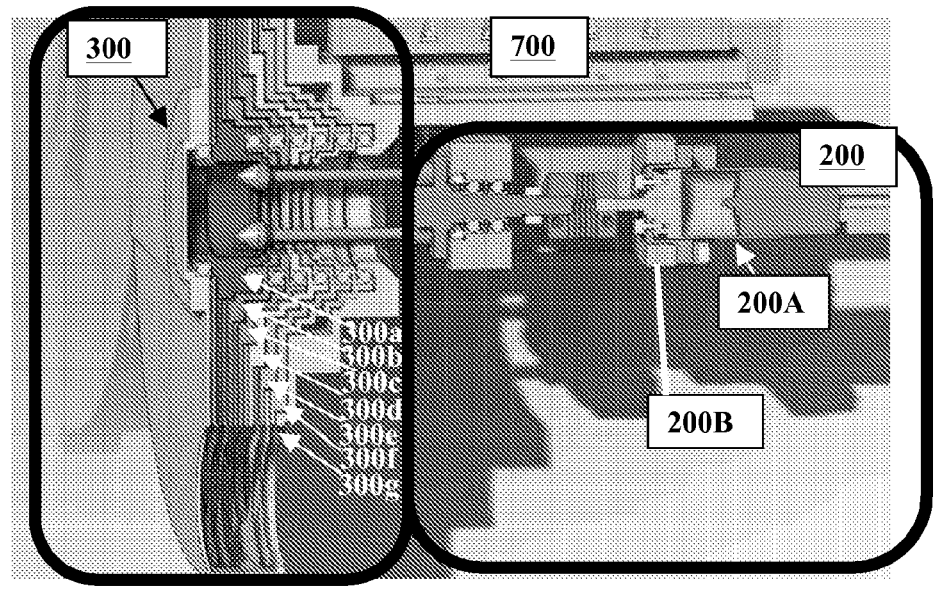

In this connection, reference is made to FIGS. 5A to 5C illustrating schematically a filter implementation system 700 configured according to an embodiment of the present invention for implementing binary spatial filters interacting with the light beam of the inspection system. Filter implementation system 700 includes a pattern generation module 200 configured for generating/selecting a binary spatial filter approximating a desired binary pattern and a filter carrier tool 300 capable of carrying the so implemented binary source mask. The filter carrier tool 300 is configured for posing the binary spatial filter within an optical path of a light beam L1 for structuring it forming the structured light L2.

In this embodiment of the invention, filter carrier tool 300 includes several filter holders 300x (e.g., 7 mask holders 300a to 300g), at least some of which are configured for carrying multiple source masks. In the present example, filter holders 300a to 300g are each configured for carrying 17 spatial filters/masks. Each of the filter holders 300x is configured and operable for interposing a filter in the propagation path of the light beam L1. The filter carrier tool 300 is implemented as a stacked array of circular filter holders 300a to 300g (e.g., sigma wheels), each carrying several static masks/filters at filter positions near its circumference. The filter holders 300a to 300g are independently rotatable about a common rotation axis and configured to enable engagement and disengagement of different filters with the optical propagation path. This allows to pattern/structure the light beam L1 utilizing various combinations of static filters from the different filter holders.

A filter holder may be configured similarly to the known in the art sigma wheel and may be capable of carrying one or more static spatial filters (typically several filters). The static spatial filters (serving as source masks for masking light from the light source) may be implemented by any suitable technique including COG and perforated foil techniques.

Optionally, the filter carrier tool 300 may be configured to enable interaction of the light beam L1 with different combinations including more than one static filter. In this manner, using different combination of filters, a pseudo dynamic spatial filter may practically be provided. The number of possible combinations of static filters is a multiplication series of the numbers of static filters carried by each filter holder. For example, in the present example, where 7 filter holders are used each carrying 17 filters, the total number of possible combinations is 17^7 which is about half a billion combinations.

It should be noted that possibly one or more of the filter holders may include/carry a neutral filter/mask which does not affect the light beam L1 interacting therewith (passing therethrough) or does not carry a filter at all at a certain filter position. Accordingly, the various combinations of static filters may also include combinations in which the number of active filters (not neutral filters) is less than the number of filter holders in the filter carrier tool 300.

As noted above, the filter implementation system 700 includes a pattern generation module 200 which is adapted for generating/implementing a spatial filter approximating a desired spatial filter pattern corresponding to an exposure condition to be emulated by the system. In the present embodiment, the pattern generation module 200 includes a control unit 200B and an actuation assembly 200A. The control unit 200B is configured to receive filter data indicative of a desired filter pattern. The filter data may be obtained in accordance with the above described technique of FIGS. 1 to 3G. Pattern generation module 200 processes the filter data, utilizing stored data indicative of the static filters mounted on the filter holders 300x, and determines a suitable combination of one or more static filters from filter holders 300a to 300g which will best approximate the desired spatial filter pattern. Control unit 200B may also be configured to utilize an appropriate algorithm (processing utility) to determine desired combination of static filters based on the received filter data. The selection of the combination of filters may also be based on tolerance data to determine which combination of static filters best emulates the desired exposure condition. The tolerance data may be similar to that described above and may for example include geometric tolerance data and transmittance tolerance data indicative of the allowable variations in the shapes and transmissions of different regions in the desired spatial pattern of the desired filter.

Having determined a desired combination of static filters, the control unit 200B may operate the actuation assembly 200A to actuate the different filter holder into desired positions in which the desired combination of static filters is engaged with the light beam's L1 propagation path. This provides patterning of the light beam L1 to form structured light L2. To this end, actuation assembly 200A may include one or more drivers or motors and possibly also a transmission/gear assembly which enable actuation of the different filter holders.

Figure 6A:
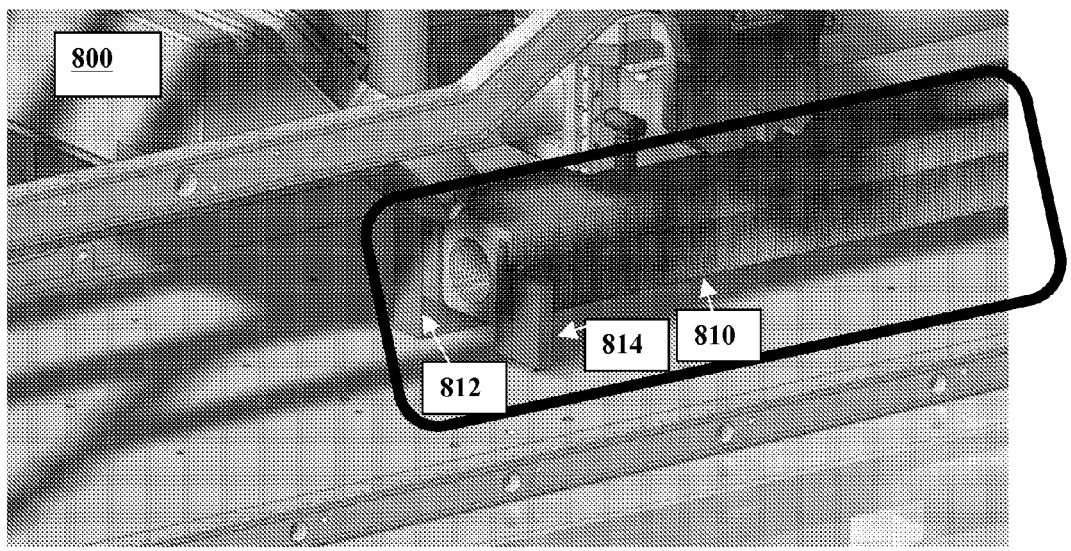
FIGS. 6A and 6B illustrate, schematically, an example of a filter implementation system configured according to another embodiment of the present invention.
Figure 6B:
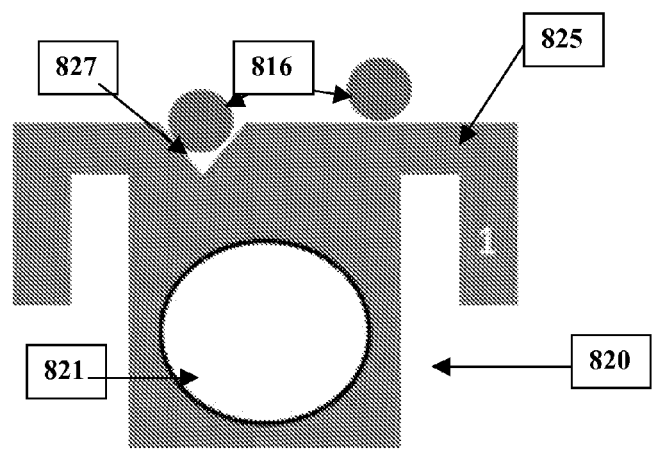

Reference is made together to FIGS. 6A and 6B schematically illustrating another example of a filter implementation system 800 configured according to an embodiment of the present invention. Here, filter implementation system 800 includes a filter carrier tool 810 capable of carrying a large number of static filters (possibly hundreds of filters) and selectively interposing a selected filter within an optical path a light beam L1 with an accurate positioning and orientation. The filter carrier tool 810 includes a cartridge slider 812 upon which multiple filters (e.g., about 200 filters in the present example) may be interchangeably arranged in a stack. The filter carrier tool 810 also includes a filter holder 814 that is located at a predetermined position with respect to the propagation path of light beam L1. The filter holder 814 is controllably actuated to engage and carry a selected filter which is mounted on the cartridge slider 812 and located at a certain respective position from the filter holder 814. Engaging with a filter, the filter holder 814 is adapted to carry the filter into the optical path of light with a certain predetermined position and orientation with respect thereto. The cartridge slider 812 is configured and operable to enable controllable actuation of the positions of the filters mounted thereon to thereby allow positioning of a selected filter to be grabbed by filter holder 814 and interacted with the light beam L1.

Filter implementation system 800 also includes alignment assembly 816 arranged in the vicinity of the light propagation path and adapted for kinematic engagement with a filter unit which is interposed by holder 814 in the optical path of L1. Engagement of the alignment assembly 816 with the filter unit 820 facilitates precise alignment of the selected filter unit 820 with respect to the light beam and thus facilitates emulation of the desired exposure condition by the filter unit 820. FIG. 6B is a schematic illustration of an example of an alignment assembly 816 including two alignment pins in kinematic engagement with a filter unit 820. The filter unit includes a frame 825 upon which a spatial filter aperture 821 is mounted and a tapered recess 827 formed on its top side. The position of the recess 827 is in accordance with the locations of the alignment pins of assembly 816 near the optical path to allow precise positioning and alignment of the filter with respect to the light beam by kinematic engagement of the alignment pins 816 with the frame 825 and recess 827.

Optionally, according to some embodiments of the invention, filter implementation system 800 may include multiple filter holders facilitating simultaneous engagement of multiple filters units with the light beam L1. Accordingly filter implementation system 800 may include a pattern generation module similar to the module 200 described with reference to FIGS. 5A to 5C. Such a pattern generation module may be configured to receive filter data indicative of a desired filter pattern and utilize stored data indicative of the filters mounted on the filter cartridge 812 to determine a suitable combination of filter units which best approximates the desired filter data. The maximal number of filters in such a combination corresponds to the number of filter holders (814) utilized in the system 800. Having determined such a suitable combination of one or more filter units, the pattern generation module may operate to actuate the cartridge 812 and the one or more filter holders (814) to interpose the combination of filters in the propagation path of light beam L1. Optionally, in such embodiments including more than one filter holders 814, alignment assembly 816 (or multiple respective alignment assemblies) may also be provided and configured to precisely position and align the filters carried by the multiple holders 814.

What is claimed is:

1. An aerial inspection system, comprising:
   an input module configured and operable for receiving intensity data indicative of an intensity distribution map corresponding to a desired exposure condition to be emulated by the aerial inspection system;
   a processing utility configured and operable for processing the intensity data and generating filter data indicative of a binary spatial filter corresponding to the intensity distribution map;
   a filter implementation unit configured and operable for receiving the filter data and generating the binary spatial filter using the filter data, the binary spatial filter comprising a plurality of static filters; and
   an filter carrier module for interacting the binary spatial filter with a light beam of the aerial inspection system to generate structured light approximating the desired exposure condition.

2. The aerial inspection system of claim 1 wherein the filter carrier module is configured and operable for carrying the plurality of static filters.

3. The aerial inspection system of claim 1 wherein the filter carrier module is configured and operable for interposing the plurality of static filters in an optical path of the light beam.

4. The aerial inspection system of claim 1 wherein the filter carrier module comprises one or more sigma wheels each for carrying at least one of the plurality of static filters.

5. The aerial inspection system of claim 1 wherein generating the binary spatial filter comprises identifying a combination of the plurality of static filters that approximates the desired exposure condition.

6. The aerial inspection system of claim 1 wherein the filter carrier module comprises a plurality of sigma wheels each for carrying one of the plurality of static filters, and interacting the binary spatial filter with the light beam comprises rotating each of the plurality of sigma wheels to interpose the plurality of static filters in an optical path of the light beam.

7. The aerial inspection system of claim 1 wherein the filter carrier module comprises a plurality of sigma wheels each for carrying one of the plurality of static filters and each being independently rotatable about a common axis.

8. The aerial inspection system of claim 1 wherein the filter carrier module comprises one or more sigma wheels each for carrying one of the plurality of static filters, and wherein at least one of the plurality of static filters is a neutral filter that does not affect the light beam.

9. The aerial inspection system of claim 1 wherein the filter carrier module comprises one or more filter holders each for carrying at least one of the plurality of static filters.

10. The aerial inspection system of claim 1 wherein the filter carrier module comprises one or more filter holders each for carrying at least one of the plurality of static filters, and wherein the filter carrier module also comprises a cartridge slider on which the plurality of static filters are mounted.

11. An aerial inspection system, comprising:
    a processing utility configured and operable for receiving data indicative of an intensity distribution map that corresponds to a desired exposure condition to be emulated by the aerial inspection system, and also configured and operable for processing the data and generating filter data indicative of a binary spatial filter corresponding to the intensity distribution map; and a filter implementation unit configured and operable for receiving the filter data and generating the binary spatial filter using a plurality of static filters, the binary spatial filter enabling the aerial inspection system to generate structured light approximating the desired exposure condition.

12. The aerial inspection system of claim 11 wherein the filter implementation unit comprises a filter carrier module configured and operable for carrying the plurality of static filters.

13. The aerial inspection system of claim 11 wherein the filter implementation unit comprises a filter carrier module configured and operable for interposing the plurality of static filters in an optical path of a light beam of the aerial inspection system.

14. The aerial inspection system of claim 11 wherein the filter implementation unit comprises a filter carrier module that includes one or more sigma wheels each for carrying at least one of the plurality of static filters.

15. The aerial inspection system of claim 11 wherein generating the binary spatial filter comprises identifying a combination of the plurality of static filters that approximates the desired exposure condition.

16. The aerial inspection system of claim 11 wherein the filter implementation unit comprises a filter carrier module that includes a plurality of sigma wheels each for carrying one of the plurality of static filters and each being independently rotatable about a common axis.

17. The aerial inspection system of claim 11 wherein the filter implementation unit comprises a filter carrier module that includes one or more sigma wheels each for carrying one of the plurality of static filters, and wherein at least one of the plurality of static filters is a neutral filter that does not affect a light beam of the aerial inspection system.

18. The aerial inspection system of claim 11 wherein the filter implementation unit comprises a filter carrier module that includes one or more filter holders each for carrying at least one of the plurality of static filters.

19. The aerial inspection system of claim 11 wherein the filter implementation unit comprises a filter carrier module that includes one or more filter holders each for carrying at least one of the plurality of static filters, and wherein the filter carrier module also comprises a cartridge slider on which the plurality of static filters are mounted.

* * * * *